(12) United States Patent
Shibata

(10) Patent No.: US 11,919,875 B2
(45) Date of Patent: Mar. 5, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventor: Natsumi Shibata, Ichihara (JP)

(73) Assignee: Resonac Corporation, Tokyo (JP)

( * ) Notice: Subject to any disclaimer, the term of this patent is extended or adjusted under 35 U.S.C. 154(b) by 103 days.

(21) Appl. No.: 17/764,386

(22) PCT Filed: Sep. 8, 2020

(86) PCT No.: PCT/JP2020/033969
§ 371 (c)(1),
(2) Date: Mar. 28, 2022

(87) PCT Pub. No.: WO2021/065382
PCT Pub. Date: Apr. 8, 2021

(65) Prior Publication Data
US 2022/0356159 A1 Nov. 10, 2022

(30) Foreign Application Priority Data
Sep. 30, 2019 (JP) .................. 2019-179774

(51) Int. Cl.
*C07D 295/088* (2006.01)
*C07C 217/08* (2006.01)
(Continued)

(52) U.S. Cl.
CPC ........ *C07D 295/088* (2013.01); *C07C 217/08* (2013.01); *C10M 105/62* (2013.01);
(Continued)

(58) Field of Classification Search
CPC ........ C10M 2213/043; C10M 2213/06; C10M 2213/0606; C10M 107/38; C10M 107/40;
(Continued)

(56) References Cited

U.S. PATENT DOCUMENTS 5,965,496 A 10/1999 Yamana et al.
6,096,694 A 8/2000 Tei et al.
(Continued)

FOREIGN PATENT DOCUMENTS

CN 107731245 A 2/2018
CN 108698968 A 10/2018
(Continued)

OTHER PUBLICATIONS

International Search Report for PCT/JP2020/033969 dated Nov. 24, 2020 [PCT/ISA/210].

*Primary Examiner* — Holly Rickman
(74) *Attorney, Agent, or Firm* — Sughrue Mion, PLLC

(57) ABSTRACT

A fluorine-containing ether compound represented by the formula (1) is provided. The fluorine-containing ether compound is represented by the following formula (1).
$R^1—R^2—CH_2—R^3—CH_2—R^4$ (1)
($R^3$ is a perfluoropolyether chain; $R^1$ is the formula (2), a in the formula (2) is an integer of 2 or 3, $R^5$ and $R^6$ are the same or different substituents. $R^5$ and $R^6$ may form a ring structure together with a nitrogen atom; $R^2$ is the formula (3), b in the formula (3) is an integer of 1 to 3; $R^4$ is a terminal group having two or three polar groups, in which individual polar groups bond to different carbon atoms and the carbon atoms to which the polar groups bond are bonded to each other through a linking group having a carbon atom to which the polar groups do not bond.)

(Continued)

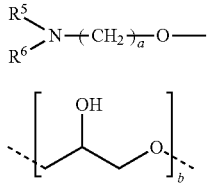

(2)

(3)

12 Claims, 1 Drawing Sheet

(51) Int. Cl.
C10M 105/62 (2006.01)
C10M 105/70 (2006.01)
C10M 107/38 (2006.01)
C10N 40/18 (2006.01)
G11B 5/725 (2006.01)

(52) U.S. Cl.
CPC ........ *C10M 105/70* (2013.01); *C10M 107/38* (2013.01); *G11B 5/7257* (2020.08); *C10M 2213/043* (2013.01); *C10M 2215/265* (2013.01); *C10M 2215/305* (2013.01); *C10N 2040/18* (2013.01)

(58) Field of Classification Search
CPC .............. C10M 107/42; C10M 107/44; C10M 2215/265; C10M 2215/305; C10M 2215/2203; C10M 2215/221; C10M 2215/223; C10M 105/62; C10M 105/70; C10M 105/60; C10M 105/54; C08G 65/007; C08G 2650/48; C10N 2040/18; G11B 5/725; G11B 5/7257; C07D 295/04; C07D 295/06; C07D 295/067; C07C 217/08

See application file for complete search history.

(56) References Cited

U.S. PATENT DOCUMENTS

| | | | |
|---|---|---|---|
| 2006/0052262 A1 | 3/2006 | Akada et al. | |
| 2012/0008228 A1* | 1/2012 | Mabuchi | G11B 5/7257 548/252 |
| 2018/0346644 A1* | 12/2018 | Guarda | C08G 65/33396 |
| 2019/0100619 A1* | 4/2019 | Tonelli | C08G 65/3255 |
| 2019/0382676 A1 | 12/2019 | Yamaguchi et al. | |
| 2023/0287288 A1* | 9/2023 | Shibata | C10M 107/38 508/182 |

FOREIGN PATENT DOCUMENTS

| | | |
|---|---|---|
| CN | 109937198 A | 6/2019 |
| JP | 11-131083 A | 5/1999 |
| JP | 2000-3512 A | 1/2000 |
| JP | 2003-82088 A | 3/2003 |
| JP | 2003-113389 A | 4/2003 |
| JP | 2006-225572 A | 8/2006 |
| JP | 2008-120714 A | 5/2008 |
| JP | 4099860 B2 | 6/2008 |
| WO | 2004/031261 A1 | 4/2004 |
| WO | 2018/139174 A1 | 8/2018 |
| WO | 2019/049585 A1 | 3/2019 |

\* cited by examiner

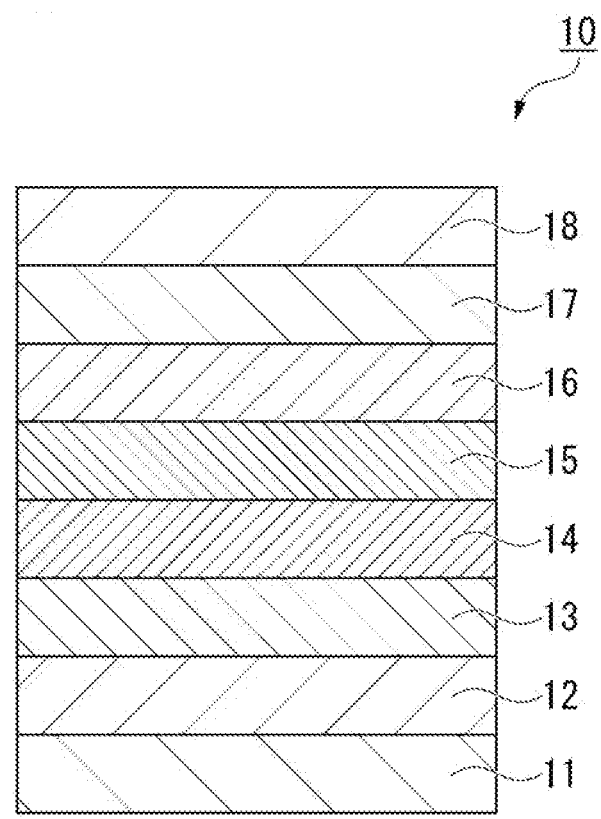

FLUORINE-CONTAINING ETHER COMPOUND, LUBRICANT FOR MAGNETIC RECORDING MEDIUM, AND MAGNETIC RECORDING MEDIUM

TECHNICAL FIELD

Cross Reference to Related Applications

This application is a National Stage of International Application No. PCT/JP2020/033969 filed Sep. 8, 2020, claiming priority based on Japanese Patent Application No. 2019-179774 filed Sep. 30, 2019, the contents of which are incorporated herein by reference.

The present invention relates to a fluorine-containing ether compound, a lubricant for a magnetic recording medium, and a magnetic recording medium.

BACKGROUND ART

Development of magnetic recording media suitable for high recording densities is underway to improve the recording densities of magnetic recording/reproducing devices.

As a conventional magnetic recording medium, there has been a magnetic recording medium in which a recording layer is formed on a substrate and a protective layer made of carbon or the like is formed on the recording layer. The protective layer protects information recorded in the recording layer and enhances the slidability of a magnetic head. However, sufficient durability of the magnetic recording medium cannot be obtained by simply providing the protective layer on the recording layer. Therefore, it is usual to apply a lubricant to the surface of the protective layer to form a lubricating layer.

As a lubricant that is used at the time of forming a lubricating layer in a magnetic recording medium, for example, a lubricant containing a compound having a polar group such as a hydroxy group or an amino group at a terminal of a fluorine-based polymer having a repeating structure containing $CF_2$ has been proposed.

For example, Patent Document 1 discloses a fluoropolyether compound having an amino alcohol group at a molecular terminal. In addition, Patent Document 2 discloses a fluorine-containing ether compound in which a group having a heterocycle ring bonds to both terminals of a perfluoropolyether chain through divalent linking groups having a polar group. In addition, Patent Document 3 discloses a fluoroether compound having amino groups having a hydroxyl group at both molecular terminals. In addition, Patent Document 4 discloses a perfluoropolyether-based liquid lubricant having an amine-based functional group in at least one of chain-like molecular terminals.

CITATION LIST

Patent Documents

Patent Document 1

Japanese Unexamined Patent Application, First Publication No. H11-131083

Patent Document 2

PCT International Publication No. WO 2018/139174

Patent Document 3

Japanese Unexamined Patent Application, First Publication No. 2006-225572

Patent Document 4

Japanese Patent No. 4099860

SUMMARY OF INVENTION

Technical Problem

There is a demand for a further decrease in the flying height of a magnetic head in magnetic recording/reproducing devices. This requires a further decrease in the thickness of lubricating layers in magnetic recording media.

However, usually, there is a tendency that a decrease in the thickness of lubricating layers degrades the coatability of the lubricating layers and thereby degrades the chemical substance resistance and wear resistance of magnetic recording media.

The present invention has been made in consideration of the above-described circumstances, and an objective of the present invention is to provide a preferable fluorine-containing ether compound as a material for lubricants for magnetic recording media capable of forming lubricating layers having excellent chemical substance resistance and wear resistance in spite of a thin thickness.

In addition, another objective of the present invention is to provide a lubricant for a magnetic recording medium that contains the fluorine-containing ether compound of the present invention and is capable of forming lubricating layers having excellent chemical substance resistance and wear resistance.

In addition, still another objective of the present invention is to provide a magnetic recording medium having a lubricating layer containing the fluorine-containing ether compound of the present invention and having excellent reliability and durability.

Solution to Problem

The present inventor repeated intensive studies to solve the above-described problems.

As a result, the present inventor found that it is preferable for fluorine-containing ether compounds to have a perfluoropolyether chain, a group having a tertiary amine bonded to a first end portion of the perfluoropolyether chain through a methylene group and a specific linking group, and a specific terminal group having two or three polar groups bonded to a second end portion through a methylene group and conceived the present invention.

That is, a first aspect of the present invention is the following fluorine-containing ether compound.

[1] A fluorine-containing ether compound represented by the following formula (1).

$$R^1-R^2-CH_2-R^3-CH_2-R^4 \tag{1}$$

(In the formula (1), $R^3$ is a perfluoropolyether chain; $R^1$ is represented by the following formula (2), a in the formula (2) is an integer of 2 or 3, in the formula (2), $R^5$ and $R^6$ are the same or different substituents, and $R^5$ and $R^6$ may form a ring structure together with a nitrogen atom; $R^2$ is represented by the following formula (3), and b in the formula (3) is an integer of 1 to 3; $R^4$ is a terminal group having two or three polar groups, in which individual polar groups bond to different carbon atoms and the carbon atoms to which the polar groups bond are bonded to each other through a linking group having a carbon atom to which the polar groups do not bond.)

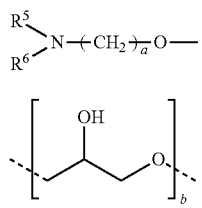

(2)

(3)

The fluorine-containing ether compound of the first aspect of the present invention may preferably have the following characteristics as described below. Two or more of the following characteristics may be preferably combined together.

[2] The fluorine-containing ether compound according to [1], in which $R^5$ and $R^6$ are each independently a saturated aliphatic group having one to four carbon atoms or $R^5$ and $R^6$ form a five to seven-membered ring together with a nitrogen atom.

[3] The fluorine-containing ether compound according to [1], in which $R^5R^6N$— in the formula (2) is a dimethylamino group or a diethylamino group.

[4] The fluorine-containing ether compound according to [1], in which $R^5R^6N$— in the formula (2) is any one group selected from a pyrrolidine group, a piperidine group, a morpholine group, and a hexamethyleneimine group.

[5] The fluorine-containing ether compound according to any one of [1] to [4], in which the $R^3$ is any of the following formulae (4) to (6).

—$CF_2O$—$(CF_2CF_2O)_c$—$(CF_2O)_d$—$CF_2$— (4)

(c and d in the formula (4) indicate average degrees of polymerization and each represents 0 to 30. Here, there is no case where c and d become 0 at the same time.)

—$CF(CF_3)$—$(OCF(CF_3)CF_2)_e$—$OCF(CF_3)$— (5)

(e in the formula (5) indicates an average degree of polymerization and represents 0.1 to 30.)

—$CF_2CF_2O$—$(CF_2CF_2CF_2O)_f$—$CF_2CF_2$— (6)

(f in the formula (6) indicates an average degree of polymerization and represents 0.1 to 30.)

[6] The fluorine-containing ether compound according to any one of [1] to [5], in which the polar group in the $R^4$ is a hydroxyl group.

[7] The fluorine-containing ether compound according to any one of [1] to [6], in which the $R^4$ is a terminal group of any of the following formulae (7) to (10).

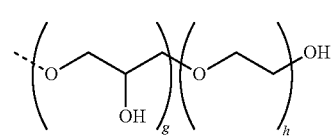

(7)

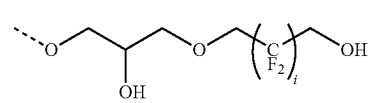

(8)

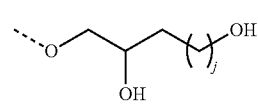

(9)

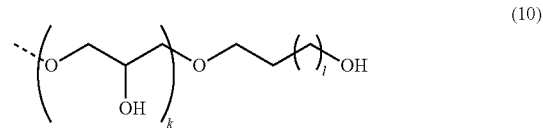

(10)

(In the formula (7), g represents an integer of 1 or 2, and h represents an integer of 1 to 5.)

(In the formula (8), i represents an integer of 2 to 5.)

(In the formula (9), j represents an integer of 1 to 5.)

(In the formula (10), k represents an integer of 1 or 2, and l represents an integer of 1 or 2.)

[8] The fluorine-containing ether compound according to any one of [1] to [7], in which a number-average molecular weight thereof is within a range of 500 to 10000.

[9] The fluorine-containing ether compound according to any one of [1] to [8], in which the compound represented by the formula (1) is any of compounds represented by the following formulae (A) to (D), (N) and (O).

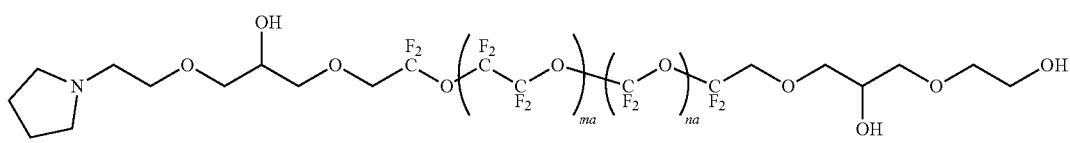

(A)

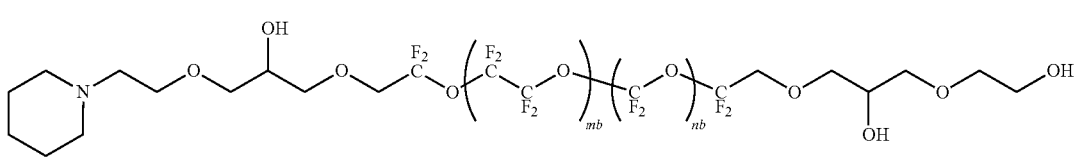

(B)

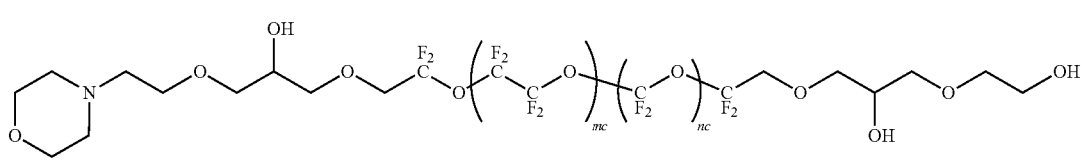

(C)

-continued

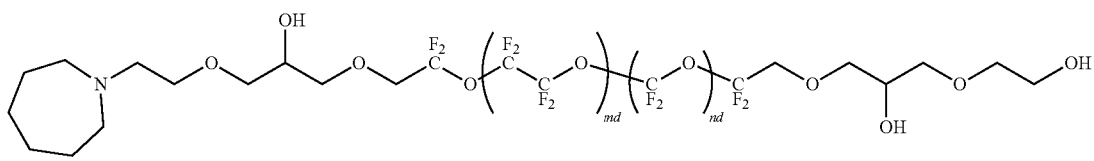
(D)

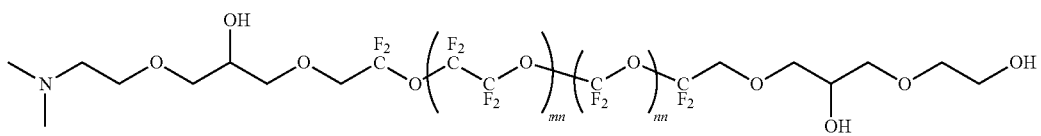
(N)

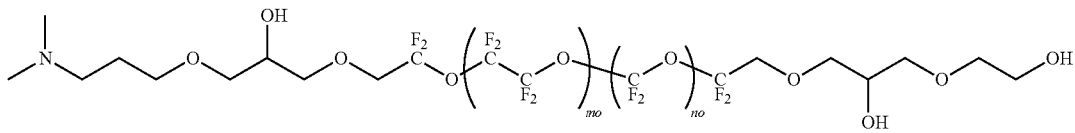
(O)

(In the formula (A), ma and na indicate average degrees of polymerization, ma represents 1 to 30, and na represents 0 to 30.)

(In the formula (B), mb and nb indicate average degrees of polymerization, mb represents 1 to 30, and rib represents 0 to 30.)

(In the formula (C), mc and nc indicate average degrees of polymerization, mc represents 1 to 30, and ne represents 0 to 30.)

(In the formula (D), md and nd indicate average degrees of polymerization, md represents 1 to 30, and nd represents 0 to 30.)

(In the formula (N), mn and nn indicate average degrees of polymerization, mn represents 1 to 30, and nn represents 0 to 30.)

(In the formula (O), mo and no indicate average degrees of polymerization, mo represents 1 to 30, and no represents 0 to 30.)

[10] A lubricant for a magnetic recording medium containing the fluorine-containing ether compound according to any one of [1] to [9].

[11] A magnetic recording medium having at least a magnetic layer, a protective layer, and a lubricating layer sequentially provided on a substrate, in which the lubricating layer contains the fluorine-containing ether compound according to any one of [1] to [9].

[12] The magnetic recording medium according to [11], in which the lubricating layer has an average film thickness of 0.5 nm to 2 nm.

Advantageous Effects of Invention

The fluorine-containing ether compound of the present invention is a compound represented by the formula (1) and is preferable as a material for lubricants for magnetic recording media.

The lubricant for a magnetic recording medium of the present invention contains the fluorine-containing ether compound of the present invention and is thus capable of forming lubricating layers from which excellent chemical substance resistance and wear resistance can be obtained in spite of a thin thickness.

The magnetic recording medium of the present invention is provided with a lubricating layer that contains the fluorine-containing ether compound of the present invention and has excellent chemical substance resistance and wear resistance and thus has excellent reliability and durability.

BRIEF DESCRIPTION OF DRAWINGS

FIG. 1 is a schematic cross-sectional view showing an embodiment of a magnetic recording medium of the present invention.

DESCRIPTION OF EMBODIMENTS

Hereinafter, preferable examples of a fluorine-containing ether compound, a lubricant for a magnetic recording medium (hereinafter, abbreviated as "lubricant" in some cases) and a magnetic recording medium of the present invention will be described in detail. The present invention is not limited only to an embodiment to be described below. Within the scope of the present invention, numbers, positions, types, quantities, ratios, combinations, numerical values, sizes, and the like can be omitted, changed and/or added as necessary.

Fluorine-Containing Ether Compound

A fluorine-containing ether compound of the present embodiment is represented by the following formula (1).

(In the formula (1), $R^3$ is a perfluoropolyether chain. $R^1$ is represented by the following formula (2). a in the formula (2) is an integer of 2 or 3. In the formula (2), $R^5$ and $R^6$ are the same or different substituents, and $R^5$ and $R^6$ may form a ring structure together with a nitrogen atom. $R^2$ is represented by the following formula (3). b in the formula (3) is an integer of 1 to 3. $R^4$ is a terminal group having two or three polar groups, in which individual polar groups bond to different carbon atoms and the carbon atoms to which the polar groups bond are bonded to each other through a linking group having a carbon atom to which the polar groups do not bond.)

(2)

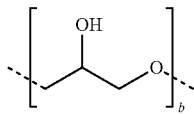

(3)

Group ($R^1$) Represented by Formula (2)

In the fluorine-containing ether compound represented by the formula (1), $R^1$ is a group represented by the formula (2) and includes a tertiary amine ($R^5R^6N$—). An unshared electron pair of the nitrogen atom that forms the tertiary amine is assumed to exhibit a favorable interaction with a protective layer, enhance the adsorption to the protective layer and improve the chemical substance resistance and wear resistance of a lubricant in a lubricating layer containing the fluorine-containing ether compound represented by the formula (1).

The nitrogen atom in the tertiary amine that is contained in $R^1$ bonds to an alkylene group (—$(CH_2)_a$—) in the formula (2). —$(CH_2)_a$—O— in the formula (2) is a divalent linking group having an ether bond, and a in the formula (2) is an integer of 2 or 3. Therefore, in the fluorine-containing ether compound represented by the formula (1), the distance between the nitrogen atom in the tertiary amine and the hydroxyl group (—OH) in $R^2$ becomes appropriate. When a in the formula (2) is 1 or 0, the fluorine-containing ether compound becomes prone to intramolecular aggregation. As a result, a lubricating layer containing this fluorine-containing ether compound is incapable of obtaining a sufficient coating rate when the thickness is made thin and is incapable of obtaining sufficient chemical substance resistance and sufficient wear resistance. In addition, when a in the formula (2) exceeds 3, since the alkylene group becomes too long, the mobility of the molecular terminal increases, and it becomes difficult to obtain the adsorption of the tertiary amine to a protective layer.

Since a in the formula (2) is an integer of 2 or 3, the fluorine-containing ether compound represented by the formula (1) is not prone to intramolecular aggregation in a lubricating layer containing the fluorine-containing ether compound and is likely to be disposed in a state of spreading and uniformly extending in the plane direction on a protective layer. Therefore, a lubricant containing the fluorine-containing ether compound represented by the formula (1) is capable of coating the surface of the protective layer at a high coating rate in spite of a thin thickness and capable of forming lubricating layers having excellent chemical substance resistance and wear resistance. a in the formula (2) is preferably 2 since the distance between the nitrogen atom in the tertiary amine and the hydroxyl group (—OH) in $R^2$ becomes more appropriate.

In addition, in the fluorine-containing ether compound represented by the formula (1), since $R^1$ and $R^2$ are bonded to each other by an ether bond (—O—) in the formula (2), the molecular structure is appropriately flexible. Therefore, in a lubricating layer containing the fluorine-containing ether compound shown by the formula (1), the interaction between $R^1$ and $R^2$ in the fluorine-containing ether compound and a protective film that is disposed in contact with the lubricating layer becomes favorable. Therefore, the lubricating layer containing the fluorine-containing ether compound is easily adsorbed to the protective layer, has excellent adhesion to the protective layer and is excellent in terms of chemical substance resistance and wear resistance.

In the fluorine-containing ether compound represented by formula (1), the structure of the tertiary amine that is included in the formula (2) can be appropriately selected depending on performance required for lubricants containing the fluorine-containing ether compound.

$R^5$ and $R^6$ in the formula (2) may be the same or different substituents. Examples of the substituents include linear, branched or cyclic saturated aliphatic groups, linear, branched or cyclic unsaturated aliphatic groups, and the like. $R^5$ and $R^6$ may form a ring structure together with the nitrogen atom.

In a case where the tertiary amine that is included in $R^1$ is an acyclic amine ($R^5$ and $R^6$ do not form a ring structure together with the nitrogen atom), specific examples of the tertiary amine ($R^5R^6N$—) in the formula (2) include a dimethylamino group, a diethylamino group, a dipropylamino group, a diisopropylamino group, a di-normal-butylamino group, a diisobutylamino group, a di-sec-butylamino group, a di-tert-butylamino group, an ethylmethylamino group, a normal-propylmethylamino group, an isopropylmethylamino group, a normal butyl methylamino group, an isobutylmethylamino group, a sec-butylmethylamino group, a tert-butylmethylamino group, an ethyl-normal-propylamine group, an ethyl isopropylamino group, an ethyl-normal-butylamino group, an ethyl isobutylamino group, a sec-butylethylamino group, a tert-butylethylamino group, an isopropylpropylamino group, a normal-butylpropylamino group, a (2-methylpropyl) (propyl) amino group, a N-sec-butylpropylamino group, a N-tert-butylpropylamino group, a N-(1-methylethyl)-1-butylamino group, a N-isopropyl-2-methyl-1-propylamino group, a N-(1-methylethyl)-2-butylamino group, a N-isopropyl-2-methyl-2-propylamino group, a butyl isobutylamino group, a butyl-sec-butylamino group, a butyl-tert-butylamino group, a N-(2-methylpropyl)-2-butylamino group, a N-(1,1-dimethylethyl)-2-methylpropylamino group, a N-(1,1-dimethylethyl)-2-butylamino group, and the like.

In a case where the tertiary amine that is included in $R^1$ is an acyclic amine ($R^5$ and $R^6$ do not form a ring structure together with the nitrogen atom). $R^5$ and $R^6$ are each preferably independently a saturated aliphatic group having one to four carbon atoms. In this case, $R^5R^6N$— in the formula (2) is appropriately bulky, whereby the fluorine-containing ether compound obtains an appropriate steric hindrance and appropriate mobility. In a case where a lubricating layer containing such a fluorine-containing ether compound is disposed on a protective layer, the lubricating layer is assumed to function as a cushion (elastic cushioning material) that mitigates an impact caused by the collision of a magnetic head with the protective layer. This prevents the magnetic head from coming too close to the protective layer and appropriately maintains the distance between the magnetic head and the protective layer. As a result, the lubricating layer containing such a fluorine-containing ether compound has a favorable affinity to the protective layer and has excellent wear resistance.

Examples of the saturated aliphatic group having one to four carbon atoms include a methyl group, an ethyl group, a normal propyl group, an isopropyl group, a normal butyl group, an isobutyl group, a sec-butyl group and a tert-butyl group. Among these, saturated aliphatic groups having one or two carbon atoms are preferable. Specifically, $R^5$ and $R^6$ are each preferably independently a methyl group or an ethyl group, and $R^5$ and $R^6$ are more preferably the same. That is, in a case where the tertiary amine that is included in $R^1$ is an acyclic amine. $R^5R^6N$— in the formula (2) is preferably any one group selected from a dimethylamino group, a methylethylamino group and a diethylamino group and more preferably a dimethylamino group or a diethylamino group since these groups are easily synthesized.

In a case where the tertiary amine that is included in $R^1$ is a cyclic amine ($R^5$ and $R^6$ form a ring structure together with the nitrogen atom), specific examples of the tertiary amine ($R^5R^6N$—) in the formula (2) include an ethyleneimine group, an azacyclobutane group, a pyrrolidine group, a piperidine group, a morpholine group, a hexamethyleneimine group, a heptamethyleneimine group, an octamethyleneimine group and the like.

In a case where the tertiary amine that is included in $R^1$ is a cyclic amine ($R^5$ and $R^6$ form a ring structure together with the nitrogen atom), the cyclic amine may have a substituent. Specific examples of the substituent include alkyl groups having a polar group and having one to three carbon atoms. In a case where the cyclic amine that is included in $R^1$ has a substituent including a polar group, examples of the polar group include a hydroxyl group, an amino group, a carboxyl group and the like, and a hydroxyl group is preferable. The bonding position of the substituent in the cyclic amine having a substituent is not particularly limited, and the substituent may bond to any of carbon atoms that configure the cyclic amine.

In a case where $R^5$ and $R^6$ form a ring structure together with the nitrogen atom, a hetoroatom other than the nitrogen atom in the tertiary amine may be included in the ring structure. Examples of the heteroatom other than the nitrogen atom in the tertiary amine include an oxygen atom, a nitrogen atom and/or the like.

In a case where the tertiary amine that is included in $R^1$ is a cyclic amine, $R^5$ and $R^6$ preferably form a five to seven-membered ring structure together with the nitrogen atom. In this case, $R^5R^6N$— in the formula (2) is appropriately bulky, whereby the fluorine-containing ether compound obtains an appropriate steric hindrance and appropriate mobility. As a result, a lubricating layer containing the fluorine-containing ether compound obtains a favorable affinity to a protective layer and obtains excellent wear resistance. Specifically, $R^5R^6N$— in the formula (2) is preferably any one group selected from a pyrrolidine group, a piperidine group, a morpholine group, and a hexamethyleneimine group. Particularly, in a case where $R^5R^6N$— in the formula (2) is a pyrrolidine group or a morpholine group, a lubricating layer having excellent wear resistance can be obtained, which is preferable.

Linking Group ($R^2$) Represented by Formula (3)

In the fluorine-containing ether compound shown in the formula (1), a divalent linking group ($R^2$) represented by the formula (3) is disposed between the group ($R^1$) represented by the formula (2) and the perfluoropolyether chain shown by $R^3$. The linking group ($R^2$) represented by the formula (3) includes one to three hydroxyl groups (—OH), which are polar groups. Due to this fact, in a lubricating layer containing the fluorine-containing ether compound of the present embodiment, a favorable interaction is generated between the lubricating layer and a protective layer, and excellent adherence (adhesion) to the protective layer can be obtained. In addition, the linking group ($R^2$) represented by the formula (3) includes an ether bond (—O—) and thus imparts appropriate flexibility to the molecular structure of the fluorine-containing ether compound shown by the formula (1). Due to these facts, compared with, for example, fluorine-containing ether compounds in which $R^1$ and $R^3$ directly bond to each other, the fluorine-containing ether compound of the present embodiment makes a lubricating layer containing the fluorine-containing ether compound easily adsorbed to a protective film and makes adhesion between the lubricating layer and the protective layer excellent.

b in the formula (3) is an integer of any of 1, 2 or 3. Since b in the formula (3) is 1 or more, in a case where a lubricating layer is formed on a protective layer using a lubricant containing the fluorine-containing ether compound shown in the formula (1), an interaction between the hydroxyl group in $R^2$ in the lubricating layer and the protective layer can be obtained. Therefore, the lubricating layer containing the fluorine-containing ether compound shown in the formula (1) is easily adsorbed to the protective layer, has excellent adhesion to the protective layer and is excellent in terms of chemical substance resistance and wear resistance. When b in the formula (3) is 2 or more, the interaction between the hydroxyl group in $R^2$ and the protective layer becomes more favorable, and the adhesion to the protective layer becomes superior. In addition, since b in the formula (3) is 3 or less, there is no case where the number of the hydroxyl groups in $R^2$ becomes too large and thus the polarity of the fluorine-containing ether compound becomes excessively high. Therefore, it is possible to prevent a lubricating layer containing the fluorine-containing ether compound from being attached to a magnetic head as foreign matter (smear) due to the excessively high polarity of the fluorine-containing ether compound, and it is possible to suppress pickup. In addition, since $R^2$ is a group represented by the formula (3), in a case where a is 2 or 3, the hydroxyl groups in $R^2$ are disposed at an appropriate distance.

Perfluoropolyether Chain Represented by $R^3$

In the fluorine-containing ether compound represented by the formula (1), $R^3$ is a perfluoropolyether chain (hereinafter, abbreviated as "PFPE chain" in some cases). The PFPE chain coats the surface of a protective layer and also imparts lubricity to a lubricating layer to reduce a frictional force between a magnetic head and the protective layer when the lubricating layer is formed by applying a lubricant containing the fluorine-containing ether compound of the present embodiment onto the protective layer. The PFPE chain is appropriately selected depending on performance or the like required for lubricants containing the fluorine-containing ether compound.

The fluorine-containing ether compound represented by the formula (1) preferably includes only one PFPE chain (only $R^3$) in the molecule. In a case where one PFPE chain is included in the molecule, no PFPE chain is included in $R^1$ and $R^4$.

Examples of the PFPE chain include PFPE chains made of a perfluoromethylene oxide polymer, a perfluoroethylene oxide polymer, a perfluoro-n-propylene oxide polymer, a perfluoroisopropylene oxide polymer, or the like, PFPE chains based on these polymers, PFPE chains made of a copolymer of monomers that configure these polymers and the like.

Specifically, $R^3$ in the formula (1) is preferably a PFPE chain represented by any of the following formulae (4) to (6). In a case where $R^3$ is any of the formulae (4) to (6), the synthesis of the fluorine-containing ether compound is easy. In a case where $R^3$ is the formula (4), the procurement of a raw material is easy, which is more preferable.

In addition, in a case where $R^3$ is any of the formulae (4) to (6), the ratio of the number of oxygen atoms (the number of ether bonds (—O—)) to the number of carbon atoms in the perfluoropolyether chain is appropriate. Therefore, the fluorine-containing ether compound becomes a compound with appropriate hardness. Therefore, the fluorine-containing ether compound applied onto a protective layer is less likely to be aggregated on the protective layer, and it is possible to form a lubricating layer having an even thinner thickness at a sufficient coating rate. In addition, in a case where $R^3$ is any of the formulae (4) to (6), the fluorine-containing ether compound becomes a compound from which lubricating layers having favorable wear resistance can be obtained.

$$—CF_2O—(CF_2CF_2O)_c—(CF_2O)_d—CF_2— \quad (4)$$

(c and d in the formula (4) indicate the average degrees of polymerization and each represents 0 to 30. Here, there is no case where c and d become 0 at the same time.)

In the formula (4), the arrangement sequence of ($CF_2$—$CF_2$—O) and ($CF_2$—O), which are repeating units, is not particularly limited. In the formula (4), the number c of ($CF_2$—$CF_2$—O)'s and the number d of ($CF_2$—O)'s may be the same or may be different from each other. Here, there is no case where c and d become 0 at the same time. The formula (4) may include any of a random copolymer, a block copolymer, and an alternating copolymer composed of the monomer units ($CF_2$—$CF_2$—O) and ($CF_2$—O).

In the formula (4), c that indicates the average degree of polymerization is 0 to 30, preferably 1 to 20 and more preferably 3 to 10. In the formula (4), d that indicates the average degree of polymerization is 0 to 30, preferably 1 to 20 and more preferably 3 to 10.

$$—CF(CF_3)—(OCF(CF_3)CF_2)_e—OCF(CF_3)— \quad (5)$$

(e in the formula (5) indicates the average degree of polymerization and represents 0.1 to 30.)

In the formula (5), e that indicates the average degree of polymerization is 0.1 to 30, preferably 1 to 30, more preferably 2 to 20 and still more preferably 3 to 10.

$$—CF_2CF_2O—(CF_2CF_2CF_2O)_f—(CF_2CF_2— \quad (6)$$

(f in the formula (6) indicates an average degree of polymerization and represents 0.1 to 30.)

In the formula (6), f that indicates the average degree of polymerization is 0.1 to 30, preferably 1 to 30, more preferably 2 to 20 and still more preferably 3 to 10.

When c, d, e and f that indicate the average degrees of polymerization in the formulae (4) to (6) are 30 or less, the viscosity of the fluorine-containing ether compound does not become too high, and lubricants containing this fluorine-containing ether compound become easy to apply, which is preferable.

Terminal Group Represented by $R^4$

In the fluorine-containing ether compound represented by the formula (1), $R^4$ is a terminal group having two or three polar groups, in which individual polar groups bond to different carbon atoms and the carbon atoms to which the polar groups bond are bonded to each other through a linking group having a carbon atom to which the polar groups do not bond. The terminal group represented by $R^4$ preferably includes no perfluoropolyether chains (PFPE chains).

The terminal group represented by $R^4$ contributes to impart adhesion between a protective layer to which a lubricant containing the fluorine-containing ether compound of the present embodiment is applied and a lubricating layer formed by applying the lubricant.

Since the number of the polar groups that are included in $R^4$ is two or three, a lubricant containing the fluorine-containing ether compound has excellent adhesion to a protective layer and is capable of forming a lubricating layer having a high coating rate. When the number of the polar groups that are included in $R^4$ is too large, the polarity of the fluorine-containing ether compound becomes too high, and thus pickup, which is the adhesion of a lubricating layer containing the fluorine-containing ether compound to a magnetic head as foreign matter (smear), is likely to occur. In the present embodiment, since the number of the polar groups that are included in $R^4$ is two or three, it is possible to suppress the occurrence of pickup arising from the excessively high polarity of the fluorine-containing ether compound.

The fluorine-containing ether compound having the terminal group represented by $R^4$ is less likely to be aggregated compared with, for example, fluorine-containing ether compounds in which two polar groups that are included in the terminal group bond to mutually different carbon atoms and the carbon atoms to which the polar groups bond are bonded to each other. Therefore, in a lubricating layer containing the fluorine-containing ether compound of the present embodiment, it is possible to prevent the fluorine-containing ether compound that exists without being attached (adsorbed) to a protective layer from being aggregated and attached to a magnetic head as foreign matter (smear), and pickup is suppressed. In addition, since the fluorine-containing ether compounds are less likely to be aggregated, the fluorine-containing ether compound in the lubricating layer is likely to be disposed in a state of spreading and extending in the plane direction on the protective layer. Therefore, it is assumed that a lubricant containing the fluorine-containing ether compound is capable of coating the surface of the protective layer at a high coating rate in spite of a thin thickness thereof and is capable of forming lubricating layers having excellent chemical substance resistance and wear resistance.

Examples of the two or three polar groups in the terminal group represented by $R^4$ include a hydroxyl group (—OH), an amino group (—$NH_2$), a carboxyl group (—COOH), a mercapto group (—SH) and the like. An ether bond (—O—) is not included in the polar groups in $R^4$. Among the above-described polar groups, the polar group is preferably a hydroxyl group. The two or three polar groups that are included in the terminal group represented by $R^4$ may be different from each other or may be all the same, but are all preferably hydroxyl groups.

The hydroxyl group has a strong interaction with a protective layer, particularly, a protective layer formed of a carbon-based material. Therefore, when some or all of the two or three polar groups in the terminal group represented by $R^4$ are hydroxyl groups, a lubricating layer containing the fluorine-containing ether compound becomes even more excellent in adhesion to protective films, which is preferable.

$R^4$ in the formula (1) can be appropriately selected depending on performance or the like required for lubricants containing the fluorine-containing ether compound. $R^4$ in the formula (1) is preferably a terminal group of any of the following formulae (7) to (10).

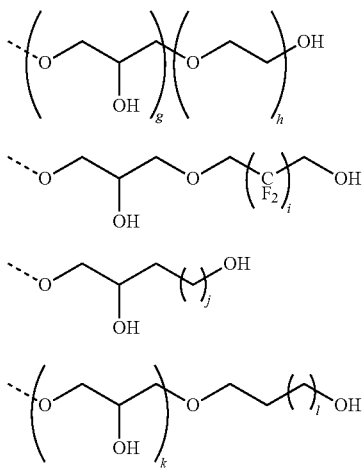

(In the formula (7), g represents an integer of 1 or 2, and h represents an integer of 1 to 5.)

(In the formula (8), i represents an integer of 2 to 5.)

(In the formula (9), j represents an integer of 1 to 5.)

(In the formula (10), k represents an integer of 1 or 2, and l represents an integer of 1 or 2.)

In the formula (7), g is an integer of 1 or 2. When g in the formula (7) is 2, adhesion to a protective layer becomes superior due to the adhesion between the hydroxyl groups in $R^2$ and the protective layer, which is preferable.

In the formula (7), h is an integer of 1 to 5. In this case, the distance between the hydroxyl groups in the terminal group represented by the formula (7) becomes appropriate, and the fluorine-containing ether compound becomes excellent in terms of adhesion to a protective layer and capable of forming a lubricating layer having a high coating rate. h is preferably 1 or 2 and most preferably 1.

In the formula (8), i is an integer of 2 to 5. In this case, the distance between the hydroxyl group on the $R^3$ side and the hydroxyl group at the terminal becomes appropriate, and the fluorine-containing ether compound becomes excellent in terms of adhesion to a protective layer and capable of forming a lubricating layer having a high coating rate. i is preferably 2 or 3 and most preferably 2.

In the formula (9), j is an integer of 1 to 5. In this case, the distance between the hydroxyl group on the $R^3$ side and the hydroxyl group at the terminal becomes appropriate, and the fluorine-containing ether compound becomes excellent in terms of adhesion to a protective layer and capable of forming a lubricating layer having a high coating rate. j is preferably 1 or 2 and most preferably 1.

In the formula (10), k represents an integer of 1 or 2, and l represents an integer of 1 or 2. In a case where k is an integer of 1 or 2 and l is an integer of 1 or 2, the distance between the hydroxyl group on the $R^3$ side and the hydroxyl group at the terminal becomes appropriate, and the fluorine-containing ether compound becomes excellent in terms of adhesion to a protective layer and capable of forming a lubricating layer having a high coating rate. k is preferably 2. l is preferably 1.

The fluorine-containing ether compound represented by the formula (1) is, specifically, preferably a compound represented by the following formulae (A) to (R). When the fluorine-containing ether compound is any of the compounds represented by the formulae (E) and (G) to (M) among these compounds, the chemical substance resistance and the wear resistance are particularly excellent, which is preferable. In addition, in all of the compounds represented by the formulae (A) to (D), (N) and (O), $R^2$ is represented by the formula (3), b in the formula (3) is 1, $R^3$ is the PFPE chain represented by the formula (4), $R^4$ is represented by the formula (7) and g and h in the formula (7) are 1. Therefore, the compounds represented by the formulae (A) to (D), (N) and (O) are easily synthesized, which is preferable.

The numbers of repetition indicated by ma to mp and na to np in the formulae (A) to (P), mq in the formula (Q) and mr in the formula (R) are values indicating the average degrees of polymerization and are not necessarily integers.

In the compounds represented by the following formulae (A) to (P), all of $R^3$'s are the PFPE chains represented by the formula (4).

In the compounds represented by the following formulae (A) to (H), all of $R^2$'s are represented by the formula (3), and b in the formula (3) is 1.

In the compounds represented by the following formulae (A) to (D), all of $R^4$'s are represented by the formula (7), and g and h in the formula (7) are 1.

In the compound represented by the following formula (A), $R^1$ is the group represented by the formula (2), and $R^5R^6N$— in the formula (2) is a pyrrolidine group. a in the formula (2) is 2.

In the compound represented by the following formula (B), $R^1$ is the group represented by the formula (2), and $R^5R^6N$— in the formula (2) is a piperidine group. a in the formula (2) is 2.

In the compound represented by the following formula (C), $R^1$ is the group represented by the formula (2), and $R^5R^6N$— in the formula (2) is a morpholine group. a in the formula (2) is 2.

In the compound represented by the following formula (D), $R^1$ is the group represented by the formula (2), and $R^5R^6N$— in the formula (2) is a hexamethyleneimine group. a in the formula (2) is 2.

In the compounds represented by the following formulae (E) to (H), all of $R^4$'s are represented by the formula (7), and, in the formula (7), g is 2 and h is 1.

In the compound represented by the following formula (E), $R^1$ is the group represented by the formula (2), and $R^5R^6N$— in the formula (2) is a pyrrolidine group. a in the formula (2) is 2.

In the compound represented by the following formula (F), $R^1$ is the group represented by the formula (2), and $R^5R^6N$— in the formula (2) is a piperidine group. a in the formula (2) is 2.

In the compound represented by the following formula (G), $R^1$ is the group represented by the formula (2), and $R^5R^6N$— in the formula (2) is a morpholine group. a in the formula (2) is 2.

In the compound represented by the following formula (H), $R^1$ is the group represented by the formula (2), and $R^5R^6N$— in the formula (2) is a hexamethyleneimine group. a in the formula (2) is 2.

In the compounds represented by the following formulae (I) to (M), all of $R^2$'s are represented by the formula (3), and b in the formula (3) is 2.

In the compounds represented by the following formulae (I) to (L), all of $R^4$'s are represented by the formula (7), and, in the formula (7), g is 2 and h is 1.

In the compound represented by the following formula (I), $R^1$ is the group represented by the formula (2), and $R^5R^6N$— in the formula (2) is a pyrrolidine group. a in the formula (2) is 2.

In the compound represented by the following formula (J), $R^1$ is the group represented by the formula (2), and $R^5R^6N$— in the formula (2) is a piperidine group. a in the formula (2) is 2.

In the compound represented by the following formula (K), $R^1$ is the group represented by the formula (2), and $R^5R^6N$— in the formula (2) is a morpholine group. a in the formula (2) is 2.

In the compound represented by the following formula (L), $R^1$ is the group represented by the formula (2), and $R^5R^6N$— in the formula (2) is a hexamethyleneimine group. a in the formula (2) is 2.

In the compound represented by the following formula (M), $R^4$ is represented by the formula (10), and, in the formula (10), k is 2 and l is 1. In the compound represented by the following formula (M), $R^1$ is the group represented by the formula (2), and $R^5R^6N$— in the formula (2) is a pyrrolidine group. a in the formula (2) is 3.

In the compounds represented by the following formulae (N) and (O), all of $R^2$'s are represented by the formula (3), and b in the formula (3) is 1. In the compounds represented by the following formulae (N) and (O), all of $R^4$'s are represented by the formula (7), and g and h in the formula (7) are 1. In the compounds represented by the following formulae (N) and (O), all of $R^1$'s are the group represented by the formula (2), and $R^5R^6N$— in the formula (2) is a dimethylamino group. In the compound represented by the following formula (N), a in the formula (2) is 2. In the compound represented by the following formula (O), a in the formula (2) is 3.

In the compound represented by the following formula (P), $R^2$ is represented by the formula (3), and b in the formula (3) is 2. In the compound represented by the following formula (P), $R^4$ is represented by the formula (7), and g and h in the formula (7) are 1. In the compound represented by the following formula (P), $R^1$ is the group represented by the formula (2), and $R^5R^6N$— in the formula (2) is a diethylamino group. a in the formula (2) is 2.

In the compounds represented by the following formulae (Q) and (R), $R^4$ is represented by the formula (7), and g and h in the formula (7) are 1.

In the compound represented by the following formula (Q), $R^3$ is the PFPE chain represented by the formula (4). In the compound represented by the following formula (Q), $R^2$ is represented by the formula (3), and b in the formula (3) is 1. In the compound represented by the following formula (Q), $R^1$ is the group represented by the formula (2), and $R^5R^6N$— in the formula (2) is a pyrrolidine group. a in the formula (2) is 2.

In the compound represented by the following formula (R), $R^3$ is the PFPE chain represented by the formula (6). In the compound represented by the following formula (R), $R^2$ is represented by the formula (3), and b in the formula (3) is 1. In the compound represented by the following formula (R), $R^1$ is the group represented by the formula (2), and $R^5R^6N$— in the formula (2) is a pyrrolidine group. a in the formula (2) is 2.

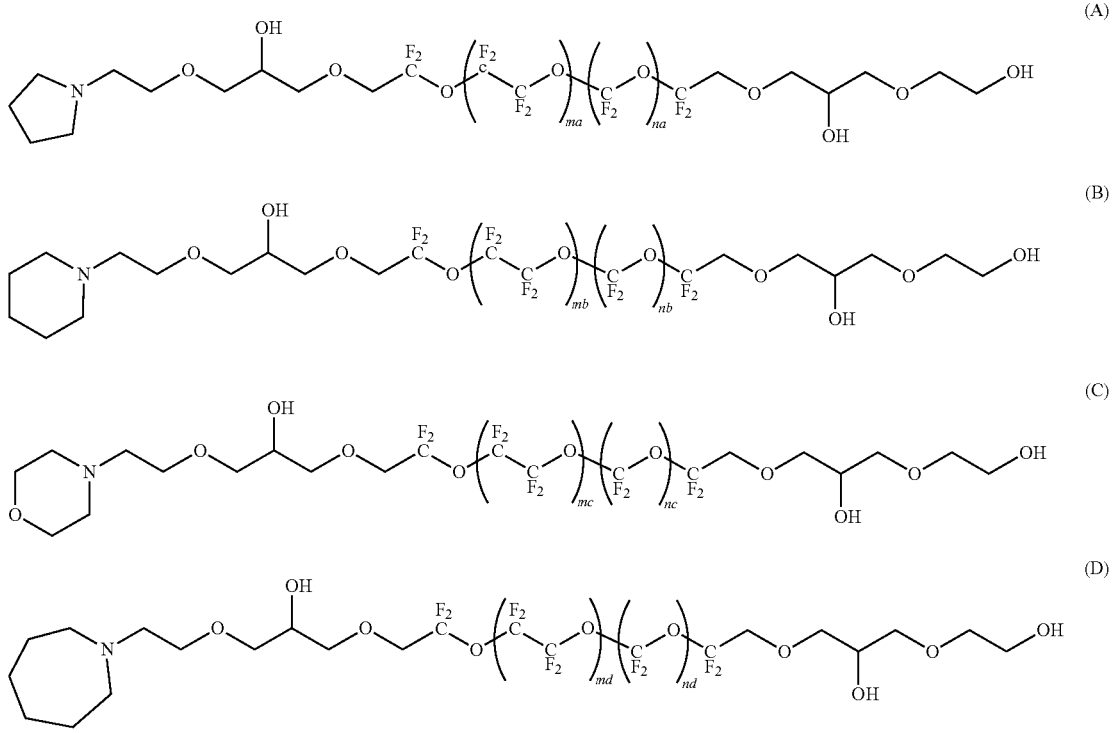

(In the formula (A), ma and na indicate the average degrees of polymerization, ma represents 1 to 30, and na represents 0 to 30.)

(In the formula (B), mb and nb indicate the average degrees of polymerization, mb represents 1 to 30, and nb represents 0 to 30.)

(In the formula (C), mc and nc indicate the average degrees of polymerization, mc represents 1 to 30, and nc represents 0 to 30.)

(In the formula (D), md and nd indicate the average degrees of polymerization, md represents 1 to 30, and nd represents 0 to 30.)

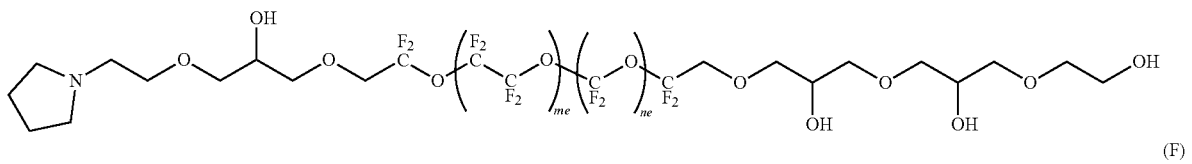

(E)

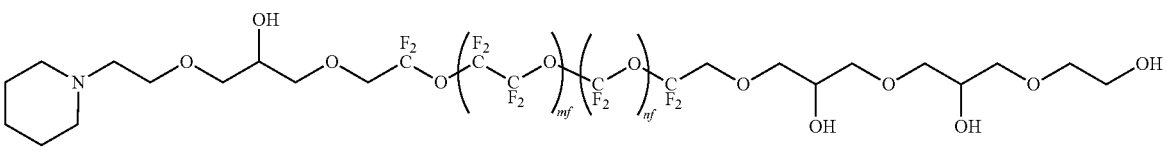

(F)

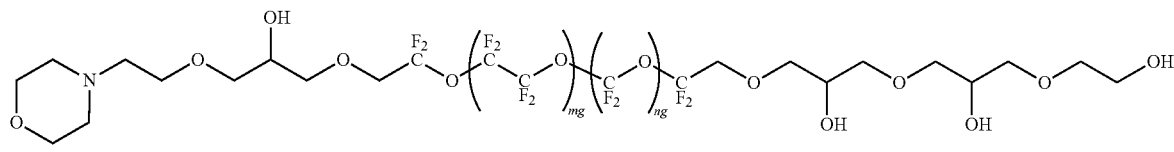

(G)

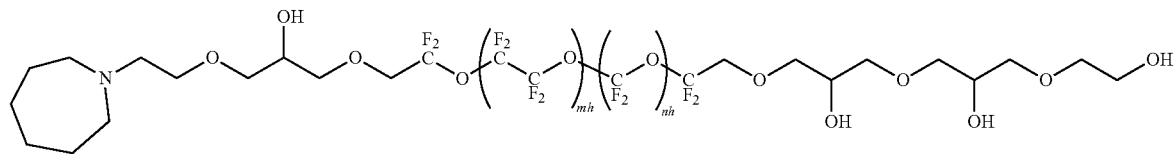

(H)

(In the formula (E), me and ne indicate the average degrees of polymerization, me represents 1 to 30, and ne represents 0 to 30.)

(In the formula (F), mf and nf indicate the average degrees of polymerization, mf represents 1 to 30, and nf represents 0 to 30.)

(In the formula (G), mg and ng indicate the average degrees of polymerization, mg represents 1 to 30, and ng represents 0 to 30.)

(In the formula (H), mh and nh indicate the average degrees of polymerization, mh represents 1 to 30, and nh represents 0 to 30.)

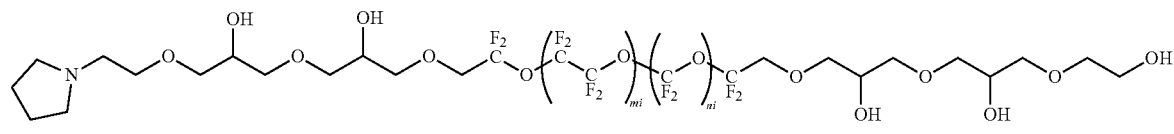

(I)

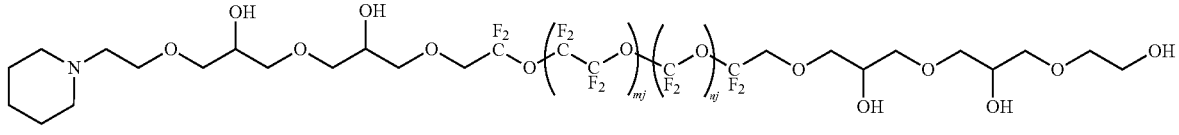

(J)

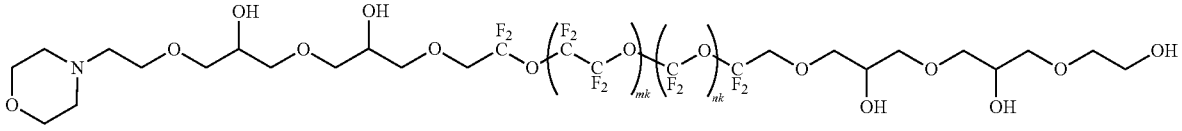

(K)

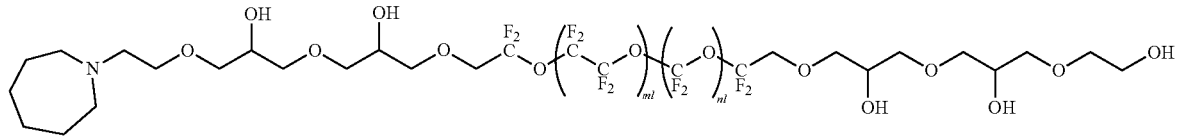

(L)

(In the formula (I), mi and ni indicate the average degrees of polymerization, mi represents 1 to 30, and ni represents 0 to 30.)

(In the formula (J), mj and nj indicate the average degrees of polymerization, mj represents 1 to 30, and nj represents 0 to 30.)

(In the formula (K), mk and nk indicate the average degrees of polymerization, mk represents 1 to 30, and nk represents 0 to 30.)

(In the formula (L), ml and nl indicate the average degrees of polymerization, ml represents 1 to 30, and nl represents 0 to 30.)

(In the formula (Q), mq indicates the average degree of polymerization, and mq represents 1 to 30.)

(In the formula (R), mr indicates the average degree of polymerization, and mr represents 1 to 30.)

In the formulae, ma to mr may be 1 to 20, may be 1 to 10, or may be 1 to 5. na to np may be 0, may be 1 to 20, may be 1 to 10, or may be 1 to 5.

When the compound represented by the formula (1) is any one of the compounds represented by the formulae (A) to (R), a raw material is easy to obtain, and furthermore, it is possible to form a lubricating layer having superior wear (M)
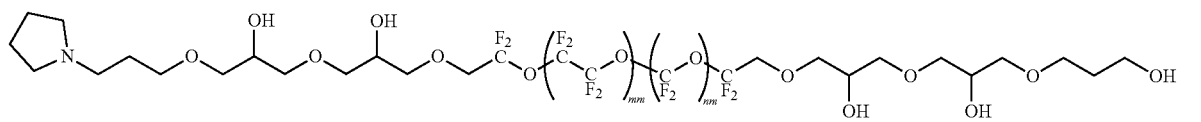

(N)
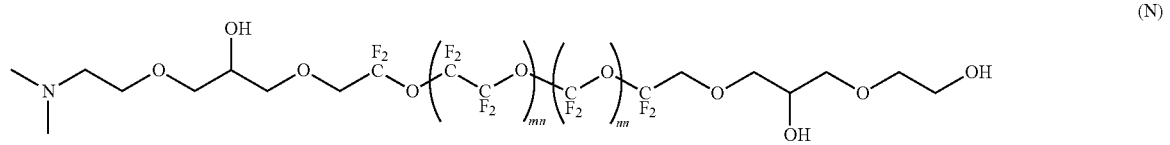

(O)
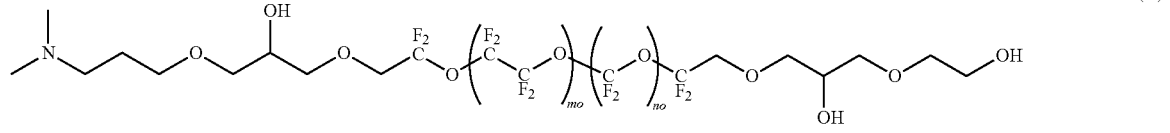

(P)
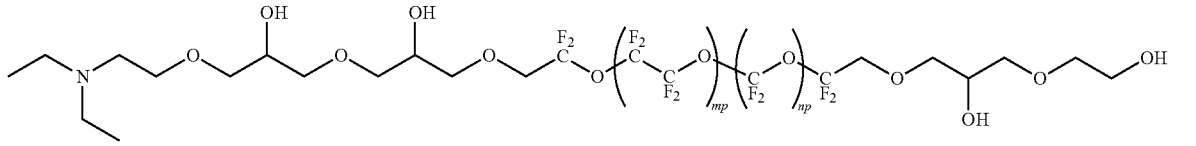

(In the formula (M), mm and nm indicate the average degrees of polymerization, mm represents 1 to 30, and nm represents 0 to 30.)

(In the formula (N), mn and nn indicate the average degrees of polymerization, mn represents 1 to 30, and nn represents 0 to 30.)

(In the formula (O), mo and no indicate the average degrees of polymerization, mo represents 1 to 30, and no represents 0 to 30.)

(In the formula (P), mp and np indicate the average degrees of polymerization, mp represents 1 to 30, and np represents 0 to 30.)

resistance and superior chemical substance resistance in spite of a thin thickness, which is preferable.

The number-average molecular weight (Mn) of the fluorine-containing ether compound of the present embodiment is preferably within a range of 500 to 10000, more preferably within a range of 700 to 7000, and particularly preferably within a range of 1000 to 3000. When the number-average molecular weight is 500 or more, lubricants containing the fluorine-containing ether compound of the present embodiment are less likely to evaporate, and it is possible to prevent the lubricants from evaporating and transferring to a magnetic head. In addition, when the (Q)
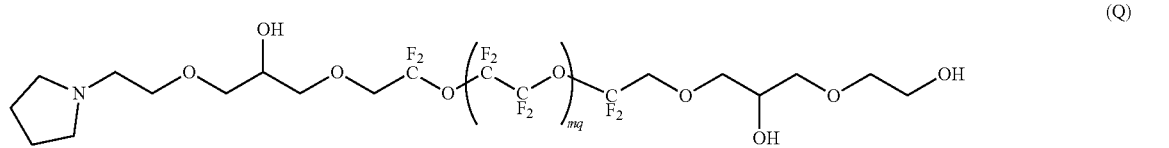

(R)
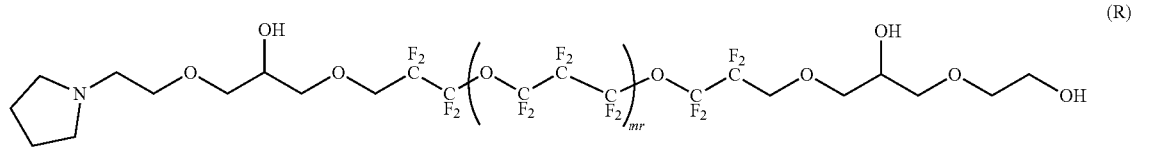

number-average molecular weight is 10000 or less, the viscosity of the fluorine-containing ether compound becomes appropriate, and application of lubricants containing this fluorine-containing ether compound makes it possible to easily form a lubricating layer having a thin thickness. When the number-average molecular weight is 3000 or less, in a case where the fluorine-containing ether compound is applied to lubricants, the viscosity of the lubricants becomes appropriate for handling, which is preferable.

The number-average molecular weight (Mn) of the fluorine-containing ether compound is a value measured by $^1$H-NMR and $^{19}$F-NMR with AVANCE III400 manufactured by Bruker BioSpin Group. In the nuclear magnetic resonance (NMR) measurement, a sample is diluted with a single or mixed solvent of hexafluorobenzene, acetone-d, tetrahydrofuran-d and the like and used in the measurement. As the reference of the $^{19}$F-NMR chemical shift, the peak of hexafluorobenzene was set to −164.7 ppm, and, as the reference of the $^1$H-NMR chemical shift, the peak of acetone was set to 2.2 ppm.

Production Method

A method for producing the fluorine-containing ether compound of the present embodiment is not particularly limited, and the fluorine-containing ether compound can be produced using a well-known conventional production method. The fluorine-containing ether compound of the present embodiment can be produced using, for example, a production method to be described below.

First, a fluorine-based compound having hydroxymethyl groups (—CH$_2$OH) disposed at both terminals of a perfluoropolyether chain corresponding to R$^3$ in the formula (3) is prepared.

Next, the hydroxyl group in the hydroxymethyl group disposed at one terminal of the fluorine-based compound is substituted with a group composed of —R$^4$ in the formula (1) (first reaction). After that, the hydroxyl group in the hydroxymethyl group disposed at the other terminal is substituted with a group composed of R$^1$—R$^2$— in the formula (1) (second reaction).

The first reaction and the second reaction can be carried out using a well-known conventional method and can be appropriately determined depending on the types of R$^1$, R$^2$ and R$^4$ in the formula (1). In addition, any reaction of the first reaction and the second reaction may be carried out earlier.

The compound represented by the formula (1) is obtained by the above-described method.

In the present embodiment, for example, in the case of producing the fluorine-containing ether compound in which R$^4$ is represented by the formulae (7) to (10), in the first reaction, the hydroxyl group in the hydroxymethyl group at one terminal of the fluorine-based compound and an epoxy compound corresponding to the formulae (7) to (10) are preferably reacted with each other.

In addition, in the second reaction, in order to introduce the group composed of R$^1$—R$^2$— into the fluorine-based compound, the hydroxyl group in the hydroxymethyl group at one terminal of the fluorine-based compound and an epoxy compound corresponding to R$^1$—R$^2$— are preferably reacted with each other.

The epoxy compound that is used at the time of producing the fluorine-containing ether compound of the present embodiment can be synthesized by, for example, reacting an alcohol having a structure corresponding to the group composed of R$^1$—R$^2$— or the terminal group represented by —R$^4$ in the fluorine-containing ether compound to be produced and any compound having an epoxy group selected from epichlorohydrin, epibromohydrin, 2-bromoethyloxirane and allyl glycidyl ether. Such an epoxy compound may be synthesized by a method of oxidizing an unsaturated bond or a commercially available product may be purchased and used.

The fluorine-containing ether compound of the present embodiment is the compound represented by the formula (1) and has the PFPE chain represented by R$^3$, the group (R$^1$) represented by the formula (2) bonded to a first end portion of R$^3$ through a methylene group (—CH$_2$—) and the linking group (R$^2$) represented by the formula (3), and the terminal group represented by R$^4$ bonded to a second end portion of R$^3$ through a methylene group (—CH$_2$—). In a lubricating layer formed on a protective layer using a lubricant containing the fluorine-containing ether compound of the present embodiment, excellent wear resistance and chemical substance resistance can be obtained by a synergistic effect of having the PFPE chain, a structure represented by R$^1$—R$^2$— and a structure represented by —R$^4$. Therefore, the lubricating layer containing the fluorine-containing ether compound of the present embodiment can be further reduced in thickness and is capable of contributing to reduction in magnetic spacing in magnetic recording media.

Specifically, the following effects <1> to <4> can be obtained by forming a lubricating layer on a protective layer using a lubricant containing the fluorine-containing ether compound of the present embodiment.

<1> Since R$^1$ is the group represented by the formula (2), and the tertiary amine (R$^5$R$^6$N—) that is included in R$^1$ has an appropriate steric hindrance, the lubricating layer containing the fluorine-containing ether compound represented by the formula (1) is capable of obtaining excellent wear resistance.

<2> Since the tertiary amine that is included in R$^1$ has appropriate mobility, the nitrogen atom in the tertiary amine can be appropriately adsorbed to the protective layer in the lubricating layer containing the fluorine-containing ether compound represented by the formula (1). As a result, excellent chemical substance resistance can be obtained.

<3> The divalent linking group (—(CH$_2$)$_a$—O—) having an ether bond is disposed between the nitrogen atom of the tertiary amine that is included in R$^1$ and R$^2$. Due to this fact, in the fluorine-containing ether compound represented by the formula (1), the distance between the nitrogen atom in the tertiary amine and the hydroxyl group (—OH) in R$^2$ becomes appropriate, which makes the fluorine-containing ether compound not prone to intramolecular aggregation. As a result, the lubricant containing the fluorine-containing ether compound of the present embodiment is capable of coating the surface of the protective layer at a high coating rate, has favorable adhesion to the protective layer and is capable of forming a lubricating layer having excellent chemical substance resistance and wear resistance. In addition, in this lubricating layer, the fluorine-containing ether compound is prevented from being aggregated and attached to a magnetic head as foreign matter (smear), and pickup is suppressed.

<4> The surface of the protective layer is coated with the PFPE chain represented by R$^3$ in the lubricating layer, and the frictional force between a magnetic head and the protective layer is reduced. Furthermore, the lubricating layer is adhered onto the protective layer by the bond between the hydroxyl group in R$^2$ linked to the first end portion of the PFPE chain represented by R$^3$ and the protective layer and the bond between the polar groups in R$^4$ linked to the second end portion of the PFPE chain and the protective layer. That is, in the fluorine-containing ether compound represented by the formula (1), since three or more polar groups including one or more hydroxyl groups in the molecule are present at appropriate positions, the interaction between the polar groups and the protective layer is effectively obtained, and the surface of the protective layer is coated at a high coating rate. Therefore, the lubricating layer containing the fluorine-containing ether compound of the present embodiment is strongly bonded to the protective layer and has excellent wear resistance and chemical substance resistance.

Lubricant for Magnetic Recording Medium

A lubricant for a magnetic recording medium of the present embodiment contains the fluorine-containing ether compound represented by the formula (1).

The lubricant of the present embodiment can be used after being mixed as necessary with a well-known material that is used as a material for lubricants as long as characteristics attributed to the fluorine-containing ether compound represented by the formula (1) contained in the lubricant are not impaired.

Specific examples of well-known materials include FOMBLIN (registered trademark) ZDIAC, FOMBLIN ZDEAL, FOMBLIN AM-2001 (all manufactured by Solvay Solexis). Moresco A20H (manufactured by Moreseo Corporation) and the like. The number-average molecular weight of the well-known material that is used by being mixed with the lubricant of the present embodiment is preferably 1000 to 10000.

In a case where the lubricant of the present embodiment contains a material other than the fluorine-containing ether compound represented by the formula (1), the content of the fluorine-containing ether compound represented by the formula (1) in the lubricant of the present embodiment is preferably 50 mass % or more and more preferably 70 mass % or more. The content of the fluorine-containing ether compound represented by formula (1) may be 80 mass % or more or 90 mass % or more. The upper limit can be arbitrarily selected and may be, for example, 99 mass % or less, 95 mass % or less or 90 mass % or less.

The lubricant of the present embodiment contains the fluorine-containing ether compound represented by the formula (1) and is thus capable of coating the surface of a protective layer at a high coating rate in spite of a thin thickness and capable of forming a lubricating layer having excellent adhesion to the protective layer. Therefore, according to the lubricant of the present embodiment, a lubricating layer having excellent chemical substance resistance and wear resistance can be obtained in spite of a thin thickness.

Magnetic Recording Medium

A magnetic recording medium of the present embodiment includes at least a magnetic layer, a protective layer and a lubricating layer sequentially provided on a substrate.

In the magnetic recording medium of the present embodiment, one or more underlayers can be provided as necessary between the substrate and the magnetic layer. In addition, it is also possible to provide an adhesive layer and/or a soft magnetic layer between the underlayer and the substrate.

FIG. 1 is a schematic cross-sectional view showing an embodiment of the magnetic recording medium of the present invention.

A magnetic recording medium 10 of the present embodiment has a structure in which an adhesive layer 12, a soft magnetic layer 15, a first underlayer 14, a second underlayer 15, a magnetic layer 16, a protective layer 17 and a lubricating layer 18 are sequentially provided on a substrate 11.

Substrate

As the substrate 11, for example, a non-magnetic substrate or the like wherein a NiP or NiP alloy film is formed on a base made of a metal or alloy material such as Al or an Al alloy can be used.

In addition, as the substrate 11, a non-magnetic substrate made of a non-metal material such as glass, ceramic, silicon, silicon carbide, carbon or resin may be used, and a non-magnetic substrate wherein a NiP or NiP alloy film is formed on a base made of this non-metal material may also be used.

Adhesive Layer

The adhesive layer 12 prevents the progress of corrosion of the substrate 11 which may occur in a case where the substrate 11 and the soft magnetic layer 13, which is provided on the adhesive layer 12, are disposed in contact with each other.

The material of the adhesive layer 12 can be appropriately selected from, for example, Cr, a Cr alloy, Ti, a Ti alloy, CrTi, NiAl, an AlRu alloy and the like. The adhesive layer 12 can be formed by, for example, a sputtering method.

Soft Magnetic Layer

The soft magnetic layer 13 preferably has a structure in which a first soft magnetic film, an interlayer made of a Ru film and a second soft magnetic film are sequentially laminated. That is, the soft magnetic layer 13 preferably has a structure in which the interlayer made of a Ru film is sandwiched between the two soft magnetic films and thereby the soft magnetic films on and under the interlayer are antiferromagnetically coupled (AFC).

Examples of the material of the first soft magnetic film and the second soft magnetic film include a CoZrTa alloy, a CoFe alloy and the like.

To the CoFe alloy that is used for the first soft magnetic film and the second soft magnetic film, any of Zr, Ta and Nb is preferably added. This accelerates the amorphization of the first soft magnetic film and the second soft magnetic film, makes it possible to improve the orientation of the first underlayer (seed layer) and makes it possible to reduce the flying height of a magnetic head.

The soft magnetic layer 13 can be formed by, for example, a sputtering method.

First Underlayer

The first underlayer 14 is a layer for controlling the orientations and/or crystal sizes of the second under layer 15 and the magnetic layer 16 that are provided on the first underlayer 14.

Examples of the first underlayer 14 include a Cr layer, a Ta layer, a Ru layer, a CrMo alloy layer, a CoW alloy layer, a CrW alloy layer, a CrV alloy layer, a CrTi alloy layer, and the like.

The first underlayer 14 can be formed by, for example, a sputtering method.

Second Underlayer

The second underlayer 15 is a layer that controls the orientation of the magnetic layer 16 to be favorable. The second underlayer 15 is preferably a Ru or Ru alloy layer.

The second underlayer 15 may be a single layer or may be composed of a plurality of layers. In a case where the second underlayer 15 is composed of a plurality of layers, all of the layers may be composed of the same material or at least one layer may be composed of a different material.

The second underlayer 15 can be formed by, for example, a sputtering method.

Magnetic Layer

The magnetic layer 16 is made of a magnetic film in which the easy magnetization axis is directed in a perpendicular or parallel direction with respect to the substrate surface. The magnetic layer 16 is, for example, a layer containing Co and Pt and may be a layer further containing an oxide or Cr, B, Cu, Ta, Zr or the like in order to improve SNR characteristics.

Examples of the oxide that is contained in the magnetic layer 16 include $SiO_2$, SiO, $Cr_2O_3$, CoO, $Ta_2O_3$, $TiO_2$ and the like.

The magnetic layer 16 may be composed of a single layer or may be composed of a plurality of magnetic layers made of materials with different compositions.

For example, in a case where the magnetic layer 16 is composed of three layers of a first magnetic layer, a second magnetic layer and a third magnetic layer sequentially laminated from below, the first magnetic layer is preferably a granular structure made of a material containing Co, Cr and Pt and further containing an oxide. As the oxide that is contained in the first magnetic layer, for example, oxides of Cr, Si, Ta, Al, Ti, Mg, Co or the like are preferably used. Among them, in particular, $TiO_2$, $Cr_2O_3$, $SiO_2$ and the like can be preferably used. In addition, the first magnetic layer is preferably made of a composite oxide to which two or more oxides have been added. Among them, in particular, $Cr_2O_3$—$SiO_2$, $Cr_2O_3$—$TiO_2$, $SiO_2$—$TiO_2$ and the like can be preferably used.

The first magnetic layer may preferably contain, in addition to Co, Cr, Pt and the oxide, one or more elements selected from B, Ta, Mo, Cu, Nd, W, Nb, Sm, Tb, Ru and Re. For the second magnetic layer, the same material as for the first magnetic layer can be used. The second magnetic layer is preferably a granular structure.

The third layer is preferably a non-granular structure made of a material containing Co, Cr and Pt but containing no oxides. The third magnetic layer may preferably contain, in addition to Co, Cr, and Pt, one or more elements selected from B, Ta, Mo, Cu, Nd, W, Nb, Sm, Tb, Ru, Re and Mn.

In a case where the magnetic layer 16 is formed of a plurality of magnetic layers, a non magnetic layer is preferably provided between the magnetic layers adjacent to each other. In a case where the magnetic layer 16 is made up of three layers of the first magnetic layer, the second magnetic layer and the third magnetic layer, it is preferable to provide a non-magnetic layer between the first magnetic layer and the second magnetic layer and a non-magnetic layer between rite second magnetic layer and the third magnetic layer.

For the non-magnetic layer that is provided between the magnetic layers adjacent to each other in the magnetic layer 16, it is possible to preferably use, for example, Ru, a Ru alloy, a CoCr alloy, a CoCrX1 alloy (X1 represents one or more elements selected from Pt, Ta, Zr, Re, Ru, Cu, Nb, Ni, Mn, Ge, Si, O, N, W, Mo, Ti, V and B) and the like.

For the non-magnetic layer that is provided between the magnetic layers adjacent to each other in the magnetic layer 16, an alloy material containing an oxide, a metallic nitride or a metallic carbide is preferably used. Specifically, as the oxide, for example, $SiO_2$, $Al_2O_3$, $Ta_2O_5$, $Cr_2O_3$, MgO, $Y_2O_3$, $TiO_2$ and the like can be preferably used. As the metallic nitride, for example, AlN, $Si_3N_4$, TaN, CrN and the like can be preferably used. As the metallic carbide, for example, TaC, BC, SiC and the like can be preferably used.

The non-magnetic layer can be formed by, for example, a sputtering method.

The magnetic layer 16 is preferably a magnetic layer for perpendicular magnetic recording in which the easy magnetization axis is directed in a direction perpendicular to the substrate surface in order to realize a higher recording density. The magnetic layer 16 may be a magnetic layer for longitudinal magnetic recording.

The magnetic layer 16 may be formed by any well-known conventional method such as a deposition method, an ion beam sputtering method or a magnetron sputtering method. The magnetic layer 16 is normally formed by a sputtering method.

Protective Layer

The protective layer 17 protects the magnetic layer 16. The protective layer 17 may be composed of a single layer or may be composed of a plurality of layers. As the material of the protective layer 17, carbon, nitrogen-containing carbon, silicon carbide and the like can be exemplified.

As the protective layer 17, a carbon-based protective layer can be preferably used, and, in particular, an amorphous carbon protective layer is preferable. When the protective layer 17 is a carbon-based protective layer, the interaction with the hydroxyl group that is included in the fluorine-containing ether compound in the lubricating layer 18 is further enhanced, which is preferable.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon based protective layer is preferably 3 to 20 atomic % when measured by the hydrogen forward scattering method (HFS). In addition, the nitrogen content in the carbon-based protective layer is preferably 4 to 15 atomic % when measured by X-ray photoelectron spectroscopy (XPS).

The hydrogen and/or nitrogen that are contained in the carbon-based protective layer do not need to be uniformly contained throughout the entire carbon based protective layer. The carbon-based protective layer is preferably formed as a composition gradient layer in which nitrogen is contained in the lubricating layer 18 side of the protective layer 17 and hydrogen is contained in the magnetic layer 16 side of the protective layer 17. In this case, the adhesive force between the magnetic layer 16 and the carbon-based protective layer and the adhesive force between the lubricating layer 18 and the carbon-based protective layer further improve.

The film thickness of the protective layer 17 can be arbitrarily selected, but is preferably set to 1 nm to 7 nm. When the film thickness of the protective layer 17 is 1 nm or more, performance as the protective layer 17 can be sufficiently obtained. The film thickness of the protective layer 17 is preferably 7 nm or less from the viewpoint of reducing the thickness of the protective layer 17.

As a method for forming the protective layer 17, it is possible to use a sputtering method in which a carbon-containing target is used, a chemical vapor deposition (CVD) method in which a hydrocarbon raw material such as ethylene or toluene is used, an ion beam deposition (IBD) method and the like.

In the case of forming a carbon-based protective layer as the protective layer 17, the carbon-based protective layer can be formed by, for example, a DC magnetron sputtering method. Particularly, in the case of forming a carbon-based protective layer as the protective layer 17, an amorphous carbon protective layer is preferably formed by a plasma CVD method. The amorphous carbon protective layer formed by the plasma CVD method has a uniform surface with small roughness.

Lubricating Layer

The lubricating layer 18 prevents contamination of the magnetic recording medium 10. In addition, the lubricating layer 18 reduces a frictional force of a magnetic head of a magnetic recording/reproducing device, which slides on the magnetic recording medium 10, and thereby improves the durability of the magnetic recording medium 10.

The lubricating layer 18 is formed in contact with the protective layer 17 as shown in FIG. 1. The lubricating layer 18 contains the above-described fluorine-containing ether compound.

In a case where the protective layer 17, which is disposed below the lubricating layer 18, is a carbon-based protective layer, particularly, the lubricating layer 18 is bonded to the protective layer 17 with a high bonding force. As a result, it becomes easy to obtain the magnetic recording medium 10 in which the surface of the protective layer 17 is coated with the lubricating layer 18 at a high coating rate in spite of a thin thickness, and it is possible to effectively prevent contamination on the surface of the magnetic recording medium 10.

The average film thickness of the lubricating layer 18 can be arbitrarily selected, but is preferably 0.5 nm (5 Å) to 2 nm (20 Å) and more preferably 0.5 nm (5 Å) to 1 nm (10 Å). When the average film thickness of the lubricating layer 18 is 0.5 nm or more, the lubricating layer 18 does not become an island shape or a mesh shape and is formed in a uniform film thickness. Therefore, the surface of the protective layer 17 can be coated with the lubricating layer 18 at a high coating rate. In addition, when the average film thickness of the lubricating layer 18 is set to 2 nm or less, it is possible to sufficiently reduce the thickness of the lubricating layer 18 and to sufficiently decrease the flying height of a magnetic head.

In a case where the surface of the protective layer 17 is not sufficiently coated with the lubricating layer 18 at a high coating rate, an environmental substance adsorbed to the surface of the magnetic recording medium 10 passes through voids in the lubricating layer 18 and intrudes into the layer below the lubricating layer 18. The environmental substance that has intruded into the layer below the lubricating layer 18 is adsorbed and bonded to the protective layer 17 and generates a contamination substance. In addition, at the time of reproducing magnetic records, this contamination substance (aggregated component) adheres (transfers) to a magnetic head as a smear to break the magnetic head or degrade the magnetic recording/reproducing characteristics of magnetic recording/reproducing devices.

Examples of the environmental substance that generates the contamination substance include siloxane compounds (cyclic siloxane and linear siloxane), ionic impurities, hydrocarbons having a relatively high molecular weight such as octacosane, plasticizers such as dioctyl phthalate and the like. Examples of a metal ion that is contained in the ionic impurities include a sodium ion, a potassium ion and the like. Examples of an inorganic ion that is contained in the ionic impurities include a chlorine ion, a bromine ion, a nitrate ion, a sulfate ion, an ammonium ion and the like. Examples of an organic ion that is contained in the ionic impurities include an oxalate ion, a formate ion and the like.

Method for Forming Lubricating Layer

A method for forming the lubricating layer 18 can be arbitrarily selected and is, for example, a method in which a magnetic recording medium that is not yet fully manufactured and thus includes the individual layers up to the protective layer 17 formed on the substrate 11 is prepared and a solution for forming the lubricating layer is applied and dried on the protective layer 17.

The solution for forming the lubricating layer can be obtained by, for example, dispersing and dissolving the above-described lubricant for a magnetic recording medium of the embodiment in a solvent as necessary and adjusting the viscosity and concentration to be suitable for application methods.

Examples of the solvent that is used for the solution for forming the lubricating layer include fluorine-based solvents such as VERTREL (registered trademark) XF (trade name, manufactured by Dupont-Mitsui Fluorochemicals Co., Ltd.) and the like.

A method for applying the solution for forming the lubricating layer is not particularly limited, and examples thereof include a spin coating method, a spraying method, a paper coating method, a dipping method and the like.

In the case of using the dipping method, it is possible to use, for example, a method to be described below. First, the substrate 11 on which the individual layers up to the protective layer 17 have been formed is immersed into the solution for forming the lubricating layer that has been put into an immersion vessel of a dip coater. Next, the substrate 11 is lifted from the immersion vessel at a predetermined speed. This applies the solution for forming the lubricating layer to the surface of the protective layer 17 on the substrate 11.

The use of the dipping method makes it possible to uniformly apply the solution for forming the lubricating layer to the surface of the protective layer 17 and makes it possible to form the lubricating layer 18 on the protective layer 17 in a uniform film thickness.

In the present embodiment, a thermal treatment is preferably carried out on the substrate 11 on which the lubricating layer 18 has been formed. The thermal treatment improves the adhesion between the lubricating layer 18 and the protective layer 17 and improves the adhesive force between the lubricating layer 18 and the protective layer 17.

The thermal treatment temperature can be arbitrarily selected, but is preferably set to 100° C. to 180° C. When the thermal treatment temperature is 100° C. or higher, an effect on improvement in the adhesion between the lubricating layer 18 and the protective layer 17 can be sufficiently obtained. In addition, when the thermal treatment temperature is set to 180° C. or lower, it is possible to prevent thermal decomposition of the lubricating layer 18. The thermal treatment time is preferably set to 10 to 120 minutes.

The magnetic recording medium 10 of the present embodiment has at least the magnetic layer 16, the protective layer 17 and the lubricating layer 18 sequentially provided on the substrate 11. In the magnetic recording medium 10 of the present embodiment, the lubricating layer 18 containing the above-described fluorine-containing ether compound is formed in contact with the protective layer 17. This lubricating layer 18 coats the surface of the protective layer 17 at a high coating rate in spite of a thin thickness. Therefore, in the magnetic recording medium 10 of the present embodiment, intrusion of the environmental substance that generates the contamination substance such as the ionic impurities through voids in the lubricating layer 18 is prevented. Therefore, the amount of the contamination substance present on the surface of the magnetic recording medium 10 of the present embodiment is small. In addition, in the lubricating layer 18 in the magnetic recording medium 10 of the present embodiment, foreign matter (smear) is less likely to be generated, and pickup can be suppressed. In addition, the lubricating layer 18 in the magnetic recording medium 10 of the present embodiment has excellent chemical substance resistance and wear resistance. Therefore, the magnetic recording medium 10 of the present embodiment has excellent reliability and durability.

(11)

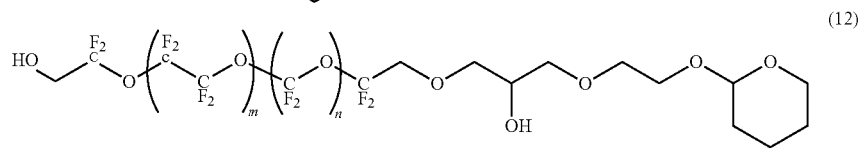

(12)

agent was filtered, the filtrate was concentrated, and the residue was purified ay silica gel column chromatography, thereby obtaining a compound represented by the following formula (12) (19.2 g, molecular weight: 1202.3, 15.9 mmol) as an intermediate.

(In the formula (12), m indicating the average degree of polymerization is 4.5, and n indicating the average degree of polymerization is 4.5.)

Next, the compound represented by the formula (12) which was the intermediate obtained above (5.95 g, molecular weight: 1202.3, 5.0 mmol), a compound represented by the following formula (13) (0.942 g, molecular weight: 171.24, 5.5 mmol) and t-butanol (2.4 mL) were charged into a 100 mL eggplant flask under a nitrogen gas atmosphere and stirred until the composition became uniform at room temperature. Potassium tert-butoxide (1.87 g, molecular weight: 112.21, 25.2 mmol) was added to this uniform liquid and reacted by being stirred at 70° C. for 22.5 hours.

EXAMPLES

Hereinafter, the present invention will be more specifically described using examples and comparative examples. The present invention is not limited only to the following examples.

Example 1

A compound represented by the formula (A) was obtained by a method to be described below.

A compound represented by $HOCH_2CF_2O(CF_2CF_2O)_m(CF_2O)_nCF_2CH_2OH$ (m indicating the average degree of polymerization in the formula was 4.5 and n indicating the average degree of polymerization was 4.5) (40 g, number-average molecular weight: 1000, molecular weight distribution: 1.1), a compound represented by the following formula (11), (4.9 g, molecular weight: 202.3, 24 mmol) and t-butanol (38 ml) were charged into a 100 ml eggplant flask under a nitrogen gas atmosphere and stirred until the composition became uniform at room temperature, thereby producing a mixture. Potassium tertbutoxide (1.4 g, molecular weight: 112.21, 12 mmol) was added to this mixture and reacted by being stirred at 70° C. for 16 hours.

The compound represented by the formula (11) used in the reaction was synthesized by oxidizing a compound obtained by protecting ethylene glycol monoallyl ether using dihydropyran.

A reaction product obtained after the reaction was cooled to 25° C., moved to a separatory funnel containing water (100 mL) and extracted three times with ethyl acetate (100 mL). An organic layer thereof was washed with water and dehydrated with anhydrous sodium sulfate. After the drying

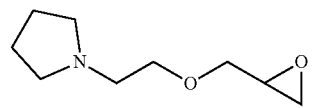

(13)

The compound represented by the formula (13) used in the reaction was synthesized by reacting epibromohydrin with the primary hydroxyl group in 1-(2-hydroxyethyl) pyrrolidine.

To a reaction solution obtained alter the reaction was returned to room temperature, a 10% hydrogen chloride/methanol solution (product name: X0041, hydrogen chloride-methanol reagent (5% to 10%), manufactured by Tokyo Chemical Industry Co., Ltd.) (26 g) was added and stirred at room temperature for 3.5 hours. The reaction solution was moved little by little to a separatory funnel containing 100 mL of saline water and extracted twice with ethyl acetate (200 mL). An organic layer thereof was sequentially washed with saline water (100 mL), saturated sodium bicarbonate water (100 mL), and saline water (100 mL) and dehydrated with anhydrous sodium sulfate. After the drying agent was filtered, the filtrate was concentrated, the residue was purified by silica gel column chromatography, thereby obtaining the compound (A) (in the formula (A), ma indicating the average degree of polymerization was 4.5 and na indicating the average degree of polymerization was 4.5) (4.25 g, molecular weight: 1289, 3.3 mmol).

$^1$H-NMR measurement of the obtained compound (A) was carried out, and the structure was identified from the following results.

Compound (A); $^1$H-NMR (CD$_3$COCD$_3$); δ[ppm]=1.78 to 1.82 (4H), 2.50 to 2.65 (6H), 3.42 to 4.50 (23H)

Example 2

The same operation as in Example 1 was carried out except that a compound represented by the following formula (14) (1.02 g) was used instead of the compound represented by formula (13), thereby obtaining the compound represented by the formula (B) (in the formula (B), mb indicating the average degree of polymerization was 4.5 and nb indicating the average degree of polymerization was 4.5) (4.30 g).

The compound represented by the formula (14) used in the reaction was synthesized by reacting epibromohydrin with the primary hydroxyl group in 1-piperidine ethanol.

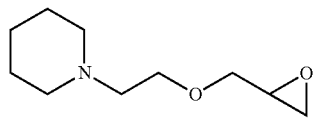

(14)

$^1$H-NMR measurement of the obtained compound (B) was carried out, and the structure was identified from the following results.

Compound (B); $^1$H-NMR (CD$_3$COCD$_3$); δ[ppm]=1.46 to 1.59 (6H), 2.53 to 2.79 (6H), 3.41 to 4.49 (23H)

Example 3

The same operation as in Example 1 was carried out except that a compound represented by the following formula (15) (1.03 g) was used instead of the compound represented by formula (13), thereby obtaining the compound represented by the formula (C) (in the formula (C), mc indicating the average degree of polymerization was 4.5 and nc indicating the average degree of polymerization was 4.5) (4.31 g).

The compound represented by the formula (15) used in the reaction was synthesized by reacting epibromohydrin with the primary hydroxyl group in 4-(2-hydroxyethyl) morpholine.

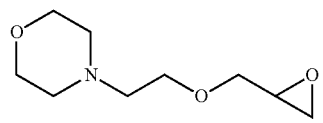

(15)

$^1$H-NMR measurement of the obtained compound (C) was carried out, and the structure was identified from the following results.

Compound (C); $^1$H-NMR (CD$_3$COCD$_3$); δ[ppm]=2.43 to 2.54 (6H), 3.40 to 4.68 (27H)

Example 4

The same operation as in Example 1 was carried out except that a compound represented by the following formula (16) (1.10 g) was used instead of the compound represented by formula (13), thereby obtaining the compound represented by the formula (D) (in the formula (D), md indicating the average degree of polymerization was 4.5 and nd indicating the average degree of polymerization was 4.5) (4.35 g).

The compound represented by the formula (16) used in the reaction was synthesized by reacting epibromohydrin with the primary hydroxyl group in hexahydro-1H-azepine-1-ethanol.

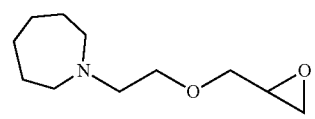

(16)

$^1$H-NMR measurement of the obtained compound (D) was carried out, and the structure was identified from the following results.

Compound (D); $^1$H-NMR (CD$_3$COCD$_3$); δ[ppm]=1.60 to 1.69 (8H), 2.50 to 2.82 (6H), 3.43 to 4.62 (23H)

Example 5

A compound represented by the formula (E) was produced by a method to be described below.

A compound represented by HOCH$_2$CF$_3$O(CF$_2$CF$_2$O)$_m$(CF$_2$O)$_n$CF$_2$CH$_2$OH (m indicating the average degree of polymerization in the formula was 4.5 and n indicating the average degree of polymerization was 4.5) (40 g, number-average molecular weight: 1000, molecular weight distribution: 1.1), a compound represented by the following formula (17), (7.69 g, molecular weight: 320.38, 24 mmol) and t-butanol (38 ml) were charged into a 100 ml eggplant flask under a nitrogen gas atmosphere and stirred until the composition became uniform at room temperature. Potassium tert-butoxide (1.4 g, molecular weight: 112.21, 12 mmol) was farther added to this uniform liquid and reacted by being stirred at 70° C. for 16 hours.

The compound represented by the formula (17) used in the reaction was synthesized using a method to be described below. A tert-butyldimethylsilyl (TBS) group was introduced as a protective group into the primary hydroxyl group in 3-allyloxy-1,2-propanediol, and a methoxymethyl (MOM) group was introduced as a protective group into the secondary hydroxyl group in the obtained compound. After that, the TBS group was removed from the compound, and 2-bromoethoxytetrahydropyran was reacted with the generated primary hydroxyl group. The double bond of the obtained compound was oxidized. The compound represented by the formula (17) was obtained by the above-described steps.

A reaction product obtained after the reaction was cooled to 25° C., moved to a separatory tunnel containing water (100 mL) and extracted three times with ethyl acetate (100 mL). An organic layer thereof was washed with water and dehydrated with anhydrous sodium sulfate. After the drying agent was filtered, the filtrate was concentrated, and the residue was purified by silica gel column chromatography, thereby obtaining a compound represented by the following formula (18) (21.00 g, molecular weight: 1320.38, 13.9 mmol) as an intermediate.

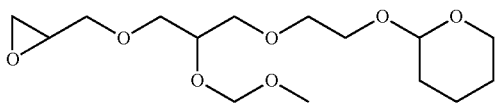

(17)

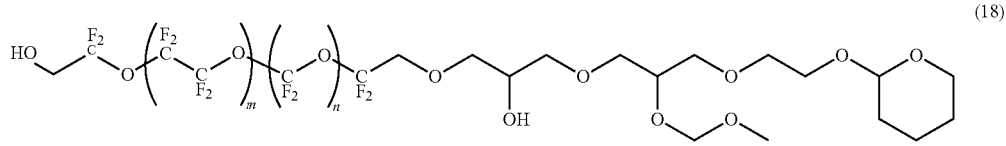

(18)

(In the formula (18), m indicating the average degree of polymerization is 4.5, and n indicating the average degree of polymerization is 4.5.)

Next, the compound represented by the formula (18) which was the intermediate obtained above (6.60 g, molecular weight: 1320.38, 5.0 mmol), a compound represented by the formula (13) (0.942 g, molecular weight: 171.24, 5.5 mmol) and t-butanol (2.4 mL) were charged into a 100 mL eggplant flask under a nitrogen gas atmosphere and stirred until the composition became uniform at room temperature. Potassium tert-butoxide (1.87 g, molecular weight: 112.21, 25.2 mmol) was added to this uniform liquid and reacted by being stirred at 70° C. for 22.5 hours.

To a reaction solution obtained after the reaction was returned to room temperature, a 10% hydrogen chloride/methanol solution (product name: X0041, hydrogen chloride-methanol reagent (5% to 10%), manufactured by Tokyo Chemical Industry Co., Ltd.) (26 g) was added and stirred at room temperature for 3.5 hours. The reaction solution was moved little by little to a separatory funnel containing 100 mL of saline water and extracted twice with ethyl acetate (200 mL). An organic layer thereof was sequentially washed with saline water (100 mL), saturated sodium bicarbonate water (100 mL), and saline water (100 mL) and dehydrated with anhydrous sodium sulfate. After the drying agent was filtered, the filtrate was concentrated, the residue was purified by silica gel column chromatography, thereby obtaining the compound (E) (in the formula (E), me indicating the average degree of polymerization was 4.5 and ne indicating the average degree of polymerization was 4.5) (4.50 g, molecular weight: 1363, 3.3 mmol).

$^1$H-NMR measurement of the obtained compound (E) was carried out, and the structure was identified from the following results.

Compound (E); $^1$H-NMR (CD$_3$COCD$_3$); δ[ppm]=1.77 to 1.82 (4H), 2.54 to 2.65 (6H), 3.42 to 4.55 (29H)

Example 6

The same operation as in Example 5 was carried out except that a compound represented by the formula (14) (1.02 g) was used instead of the compound represented by formula (13), thereby obtaining the compound represented by the formula (F) (in the formula (F), mf indicating the average degree of polymerization was 4.5 and nf indicating the average degree of polymerization was 4.5) (4.55 g).

$^1$H-NMR measurement of the obtained compound (F) was carried out, and the structure was identified from the following results.

Compound (F); $^1$H-NMR (CD$_3$COCD$_3$); δ[ppm]=1.45 to 1.60 (6H), 2.51 to 2.69 (6H), 3.41 to 4.52 (29H)

Example 7

The same operation as in Example 5 was carried out except that a compound represented by the formula (15) (1.03 g) was used instead of the compound represented by formula (13), thereby obtaining the compound represented by the formula (G) (in the formula (G), mg indicating the average degree of polymerization was 4.5 and ng indicating the average degree of polymerization was 4.5) (4.55 g).

$^1$H-NMR measurement of the obtained compound (G) was carried out, and the structure was identified from the following results.

Compound (G); $^1$H-NMR (CD$_3$COCD$_3$); δ[ppm]=2.42 to 2.53 (6H), 3.40 to 4.70 (33H)

Example 8

The same operation as in Example 5 was carried out except that a compound represented by the formula (16) (1.03 g) was used instead of the compound represented by formula (13), thereby obtaining the compound represented by the formula (H) (in the formula (H), mh indicating the average degree of polymerization was 4.5 and nh indicating the average degree of polymerization was 4.5) (4.55 g).

$^1$H-NMR measurement of the obtained compound (H) was carried out, and the structure was identified from the following results.

Compound (H); $^1$H-NMR (CD$_3$COCD$_3$); δ[ppm]=1.56 to 1.68 (8H), 2.44 to 2.77 (6H), 3.42 to 4.71 (29H)

Example 9

The same operation as in Example 5 was carried out except that a compound represented by the following formula (19) (1.81 g) was used instead of the compound represented by formula (13), thereby obtaining the compound represented by the formula (I) (in the formula (I), mi indicating the average degree of polymerization was 4.5 and ni indicating the average degree of polymerization was 4.5) (4.74 g).

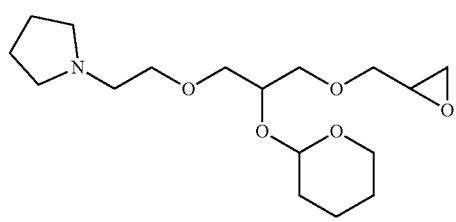

(19)

The compound represented by the formula (19) used in the reaction was synthesized using a method to be described below. Allyl glycidyl ether was reacted with the primary hydroxyl group in 1-(2-hydroxyethyl)pyrrolidine. The secondary hydroxyl group in the obtained compound was protected with a tetrahydropyranyl (THP) group, and the terminal double bond of the obtained compound was oxidized. The compound represented by the formula (19) was obtained by the above-described steps.

¹H-NMR measurement of the obtained compound (I) was carried out, and the structure was identified from the following results.

Compound (I); ¹H-NMR (CD$_3$COCD$_3$); δ[ppm]=1.76 to 1.82 (4H), 2.50 to 2.63 (6H), 3.42 to 4.65 (35H)

Example 10

The same operation as in Example 5 was carried out except that a compound represented by the following formula (20) (1.89 g) was used instead of the compound represented by formula (13), thereby obtaining the compound represented by the formula (J) (in the formula (J), mj indicating the average degree of polymerization was 4.5 and nj indicating the average degree of polymerization was 4.5) (4.79 g).

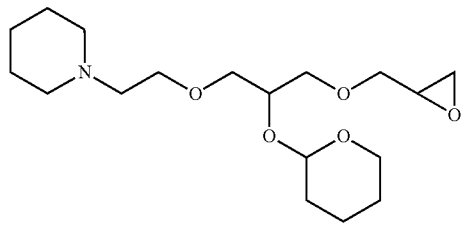

(20)

The compound represented by the formula (20) used in the reaction was synthesized using a method to be described below. Allyl glycidyl ether was reacted with the primary hydroxyl group in 1-piperidine ethanol. The secondary hydroxyl group in the obtained compound was protected with a THP group, and the terminal double bond of the obtained compound was oxidized. The compound represented by the formula (20) was obtained by the above-described steps.

¹H-NMR measurement of the obtained compound (J) was carried out, and the structure was identified from the following results.

Compound (J); ¹H-NMR (CD$_3$COCD$_3$); δ[ppm]=1.45 to 1.59 (6H), 2.57 to 2.78 (6H), 3.42 to 4.54 (35H)

Example 11

The same operation as in Example 5 was carried out except that a compound represented by the following formula (21) (1.90 g) was used instead of the compound represented by formula (13), thereby obtaining the compound represented by the formula (K) (in the formula (K), mk indicating the average degree of polymerization was 4.5 and nk indicating the average degree of polymerization was 4.5) (4.80 g).

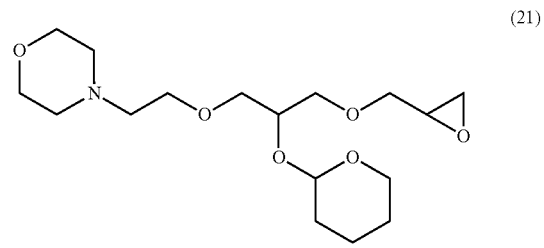 [SMILES: C1CCC(OC(COCCN2CCOCC2)COCC2CO2)OC1]

(21)

The compound represented by the formula (21) used in the reaction was synthesized using a method to be described below. Allyl glycidyl ether was reacted with the primary hydroxyl group in 4-(2-hydroxyethyl)morpholine. The secondary hydroxyl group in the obtained compound was protected with a THP group, and the terminal double bond of the obtained compound was oxidized. The compound represented by the formula (21) was obtained by the above-described steps.

¹H-NMR measurement of the obtained compound (K) was carried out, and the structure was identified from the following results.

Compound (K); ¹H-NMR (CD$_3$COCD$_3$); δ[ppm]=2.47 to 2.55 (6H), 3.46 to 4.76 (39H)

Example 12

The same operation as in Example 5 was carried out except that a compound represented by the following formula (22) (2.00 g) was used instead of the compound represented by formula (13), thereby obtaining the compound represented by the formula (L) (in the formula (L), ml indicating the average degree of polymerization was 4.5 and nl indicating the average degree of polymerization was 4.5) (4.84 g).

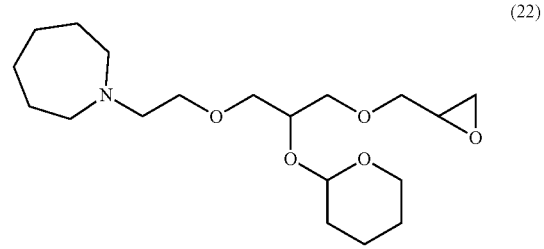 [SMILES: C1CCCN(CCOCC(COCC2CO2)OC2CCCCO2)CC1]

(22)

The compound represented by the formula (22) used in the reaction was synthesized using a method to be described below. Allyl glycidyl ether was reacted with the primary hydroxyl group in hexahydro-1H-azepine-1-ethanol. The secondary hydroxyl group in the obtained compound was protected with a THP group, and the terminal double bond of the obtained compound was oxidized. The compound represented by the formula (22) was obtained by the above-described steps.

¹H-NMR measurement of the obtained compound (L) was carried out, and the structure was identified from the following results.

Compound (L); ¹H-NMR (CD$_3$COCD$_3$); δ[ppm]=1.52 to 1.63 (8H), 2.46 to 2.80 (6H), 3.40 to 4.68 (35H)

Example 13

A compound represented by the formula (M) was produced by a method to be described below.

A compound represented by $HOCH_2CF_2O(CF_2CF_2O)_m(CF_3O)_nCF_2CH_2OH$ (m indicating the average degree of polymerization in the formula was 4.5 and n indicating the average degree of polymerization was 4.5) (40 g, number-average molecular weight: 1000, molecular weight distribution: 1.1), a compound represented by the following formula (23), (8.03 g, molecular weight: 334.41, 24 mmol) and t-butanol (38 ml) were charged into a 100 ml eggplant flask under a nitrogen gas atmosphere and stirred until the composition became uniform at room temperature. Potassium tert-butoxide (1.4 g, molecular weight: 112.21, 12 mmol) was further added to this uniform liquid and reacted by being stirred at 70° C. for 16 hours.

The compound represented by the formula (23) used in the reaction was synthesized using a method to be described below. A tert-butyldimethylsilyl (TBS) group was introduced as a protective group into the primary hydroxyl group in 3-allyloxy-1,2-propanediol, and a methoxymethyl (MOM) group was introduced as a protective group into the secondary hydroxyl group in the obtained compound. After that, the TBS group in the obtained compound was removed, and 2-(chloropropoxy)tetrahydro-2H-pyran was reacted with the generated primary hydroxyl group. The double bond of the obtained compound was oxidized. The compound represented by the formula (23) was obtained by the above-described steps.

A reaction product obtained after the reaction was cooled to 25° C., moved to a separatory tunnel containing water (100 mL) and extracted three times with ethyl acetate (100 mL). An organic layer thereof was washed with water and dehydrated with anhydrous sodium sulfate. After the drying agent was filtered, the filtrate was concentrated, and the residue was purified by silica gel column chromatography, thereby obtaining a compound represented by the following formula (24) (21.27 g, molecular weight: 1334.41, 15.9 mmol) as an intermediate.

atmosphere and stirred until the composition became uniform at room temperature. Potassium tert-butoxide (1.87 g, molecular weight: 112.21, 25.2 mmol) was added to this uniform liquid and reacted by being stirred at 70° C. for 22.5 hours.

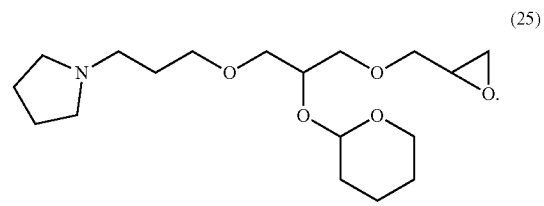 [SMILES: C1CCC(OC(COCCCN2CCCC2)COCC2CO2)OC1]

(25)

The compound represented by the formula (25) used in the reaction was synthesized using a method to be described below. Allyl glycidyl ether was reacted with the primary hydroxyl group in 1-(3-hydroxypropyl)pyrrolidine. The secondary hydroxyl group in the obtained compound was protected with a tetrahydropyranyl (THP) group, and the terminal double bond of the obtained compound was oxidized. The compound represented by the formula (25) was obtained by the above-described steps.

To a reaction solution obtained after the reaction was returned to room temperature, a 10% hydrogen chloride/methanol solution (product name: X0041, hydrogen chloride-methanol reagent (5% to 10%), manufactured by Tokyo Chemical Industry Co., Ltd.) (26 g) was added and stirred at room temperature for 3.5 hours. The reaction solution was moved little by little to a separatory funnel containing 100 mL of saline water and extracted twice with ethyl acetate (200 mL). An organic layer thereof was sequentially washed with saline water (100 mL), saturated sodium bicarbonate water (100 mL), and saline water (100 mL) and dehydrated with anhydrous sodium sulfate. After the drying agent was filtered, the filtrate was concentrated, the residue was purified by silica gel column chromatography, thereby obtaining the compound (M) (in the formula (M), mm indicating the

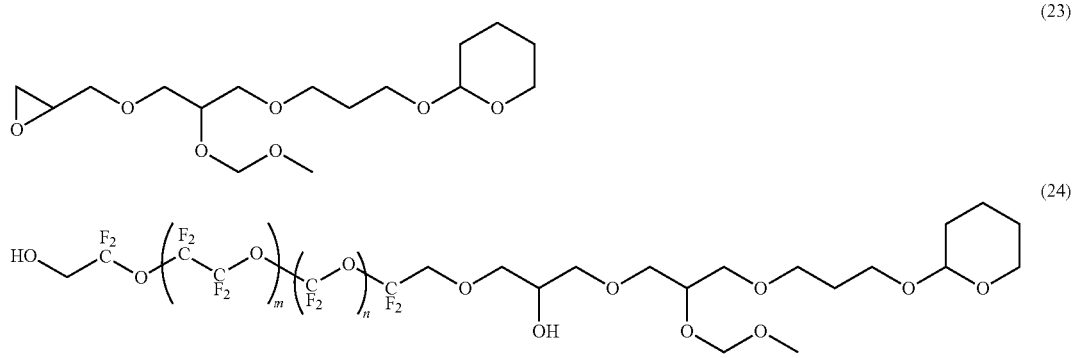

(In the formula (24), m indicating the average degree of polymerization is 4.5, and n indicating the average degree of polymerization is 4.5.)

Next, the compound represented by the formula (24), which was the intermediate obtained above, (6.67 g, molecular weight: 1334.41, 5.0 mmol), a compound represented by the following formula (25) (1.80 g, molecular weight: 343.46, 5.5 mmol) and t-butanol (2.4 mL) were charged into a 100 mL eggplant flask under a nitrogen gas average degree of polymerization was 4.5 and nm indicating the average degree of polymerization was 4.5) (4.84 g, molecular weight: 1466, 3.3 mmol).

$^1$H-NMR measurement of the obtained compound (M) was carried out, and the structure was identified from the following results.

Compound (M); $^1$H-NMR ($CD_3COCD_3$); δ[ppm]=1.62 to 1.68 (2H), 1.75 to 1.80 (4H), 2.51 to 2.59 (6H), 3.46 to 4.66 (37H)

Example 14

A compound represented by the following formula (N) was synthesized by the following method.

The same operation as in Example 1 was carried out except that a compound represented by the following formula (26) (0.80 g) was used instead of the compound represented by formula (13), thereby obtaining the compound represented by the formula (N) (in the formula (N), mn indicating the average degree of polymerization was 4.5 and nn indicating the average degree of polymerization was 4.5) (4.17 g).

The compound represented by the formula (26) used in the reaction was synthesized by reacting epibromohydrin with the primary hydroxyl group in 2-(dimethylamino) ethanol.

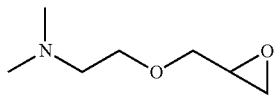
(26)

$^1$H-NMR measurement of the obtained compound (N) was carried out, and the structure was identified from the following results.

Compound (N); $^1$H-NMR (CD$_3$COCD$_3$); δ[ppm]=2.27 (6H), 2.45 to 2.48 (2H), 3.42 to 4.60 (23H)

Example 15

A compound represented by the following formula (O) was synthesized by the following method.

The same operation as in Example 1 was carried out except that a compound represented by the following formula (27) (0.88 g) was used instead of the compound represented by formula (13), thereby obtaining the compound represented by the formula (O) (in the formula (O), mo indicating the average degree of polymerization was 4.5 and no indicating the average degree of polymerization was 4.5) (4.22 g).

The compound represented by the formula (27) used in the reaction was synthesized by reacting epibromohydrin with the primary hydroxyl group in 3-(dimethylamino)-1-propanol.

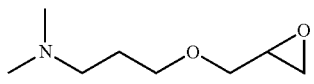
(27)

$^1$H-NMR measurement of the obtained compound (O) was carried out, and the structure was identified from the following results.

Compound (O); $^1$H-NMR (CD$_3$COCD$_3$); δ[ppm]=1.66 to 1.69 (2H), 2.27 (6H), 2.51 to 2.53 (2H), 3.49 to 4.60 (23H)

Example 16

A compound represented by the following formula (P) was synthesized by the following method.

The same operation as in Example 1 was carried out except that a compound represented by the following formula (28) (1.82 g) was used instead of the compound represented by formula (13), thereby obtaining the compound represented by the formula (P) (in the formula (P), mp indicating the average degree of polymerization was 4.5 and np indicating the average degree of polymerization was 4.5) (4.51 g).

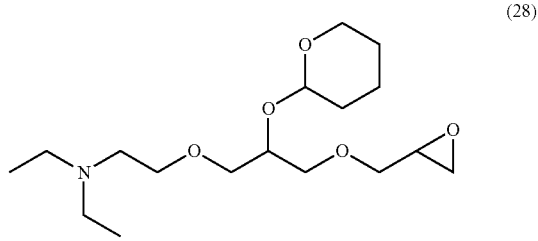 [SMILES: CCN(CC)CCOCC(COCC1CO1)OC1CCCCO1]
(28)

The compound represented by the formula (28) used in the reaction was synthesized using a method to be described below. Allyl glycidyl ether was reacted with the primary hydroxyl group in 2-diethylaminoethanol. The secondary hydroxyl group in the obtained compound was protected with a tetrahydropyranyl (THP) group, and the terminal double bond of the obtained compound was oxidized. The compound represented by the formula (28) was obtained by the above-described steps.

$^1$H-NMR measurement of the obtained compound (P) was carried out, and the structure was identified from the following results.

Compound (P); $^1$H-NMR (CD$_3$COCD$_3$); δ[ppm]=1.03 (6H), 2.50 to 2.58 (6H), 3.42 to 4.68 (29H)

Example 17

A compound represented by the formula (Q) was obtained by a method to be described below.

The same operation as in Example 1 was carried out except that a compound represented by HOCH$_2$CF$_2$O(CF$_2$CF$_2$O)$_s$CF$_2$CH$_2$OH (s indicating the average degree of polymerization in the formula was 7.1) (40 g) was used instead of the compound represented by HOCH$_2$CF$_2$O(CF$_2$CF$_2$O)$_m$(CF$_2$O)$_n$CF$_2$CH$_2$OH (m indicating the average degree of polymerization in the formula was 4.5 and n indicating the average degree of polymerization was 4.5), thereby obtaining the compound represented by the formula (Q) (in the formula (Q), mq indicating the average degree of polymerization was 7.1) (4.25 g).

Example 18

A compound represented by the formula (R) was obtained by a method to be described below.

The same operation as in Example 1 was carried out except that a compound represented by HOCH$_2$CF$_2$CF$_2$(OCF$_2$CF$_2$CF$_2$)$_t$OCF$_2$CF$_2$CH$_2$OH (t indicating the average degree of polymerization in the formula was 4.4) (40 g) was used instead of the compound represented by HOCH$_2$CF$_2$O(CF$_2$CF$_2$O)$_m$(CF$_2$O)$_n$CF$_2$CH$_2$OH (m indicating the average degree of polymerization in the formula was 4.5 and n indicating the average degree of polymerization was 4.5), thereby obtaining the compound represented by the formula (R) (in the formula (R), mr indicating the average degree of polymerization was 4.4) (4.25 g).

Comparative Example 1

A compound represented by the following formula (S) was synthesized by the following method.

The same operation as in Example 1 was carried out except that a compound represented by the following formula (29) (0.99 g) was used instead of the compound represented by formula (13), thereby obtaining a compound represented by the following formula (S) (4.28 g).

The compound represented by the formula (29) used in the reaction was synthesized by reacting epibromohydrin with the primary hydroxyl group in pyridine-4-ethanol.

bonate water (100 mL), and saline water (100 mL) and dehydrated with anhydrous sodium sulfate. After the drying agent was filtered, the filtrate was concentrated.

A 10% hydrogen chloride/methanol solution (product name: X0041, hydrogen chloride-methanol reagent (5% to 10%), manufactured by Tokyo Chemical Industry Co., Ltd.) (26 g) was added to the concentrated filtrate and stirred at room temperature for 3.5 hours. The reaction solution was moved little by little to a separatory funnel containing 100 mL of saline water and extracted twice with ethyl acetate

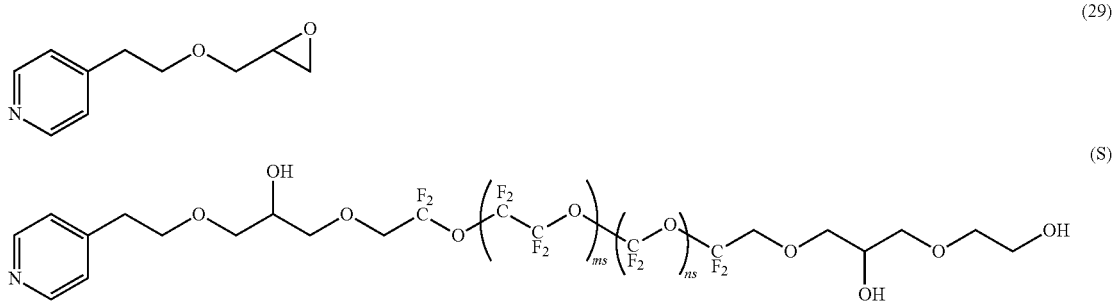

(In the formula (S), ms indicating the average degree of polymerization is 4.5, and ns indicating the average degree of polymerization is 4.5.)

$^1$H-NMR measurement of the obtained compound (S) was carried out, and the structure was identified from the following results.

Compound (S); $^1$H-NMR (CD$_3$COCD$_3$); δ[ppm]=2.82 to 2.85 (2H), 3.39 to 4.66 (23H), 7.39 to 8.63 (4H)

(200 mL). An organic layer thereof was sequentially washed with saline water (100 mL), saturated sodium bicarbonate water (100 mL), and saline water (100 mL) and dehydrated with anhydrous sodium sulfate. After the drying agent was filtered, the filtrate was concentrated, and the residue was purified by silica gel column chromatography, thereby obtaining a compound (T) (3.98 g, molecular weight: 1205, 3.3 mmol).

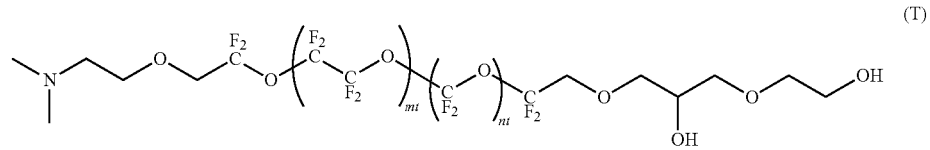

Comparative Example 2

A compound represented by the following formula (T) was synthesized by the following method.

The compound represented by the formula (12), which was the intermediate produced in Example 1 (5.95 g, molecular weight: 1202.3, 5.0 mmol), 60% sodium hydride (0.40 g, molecular weight: 24.0, 10.0 mmol) and N,N-dimethylformamide (2.4 mL) were charged into a 100 mL eggplant flask under a nitrogen gas atmosphere and stirred until the composition became uniform at room temperature. 2-Chloro-N,N-dimethylethylamine (0.59 g, molecular weight: 107.58, 5.5 mmol) was added to this uniform liquid and reacted by being stirred at 70° C. for 22.5 hours.

To a reaction solution obtained after the reaction was returned to room temperature, water was added and stirred at room temperature for 10 minutes. The reaction solution was moved little by little to a separatory funnel containing 100 mL of saline water and extracted twice with ethyl acetate (200 mL). An organic layer thereof was sequentially washed with saline water (100 mL), saturated sodium bicar- (In the formula (T), mt indicating the average degree of polymerization is 4.5, and nt indicating the average degree of polymerization is 4.5.)

$^1$H-NMR measurement of the obtained compound (T) was carried out, and the structure was identified front the following results.

Compound (T); $^1$H-NMR (CD$_3$COCD$_3$); δ[ppm]=2.26 (6H), 2.43 to 2.46 (2H), 3.45 to 4.64 (17H)

Comparative Example 3

A compound represented by the following formula (U) was synthesized by the method described in the examples of Patent Document 1.

A compound represented by the following formula (30) having glycidyl groups at the molecular terminal (4.12 g) was obtained from HOCH$_2$CF$_2$O(CF$_2$CF$_2$O)$_m$(CF$_2$O)$_n$CF$_2$CH$_2$OH (m indicating the average degree of polymerization in the formula was 4.5 and n indicating the average degree of polymerization was 4.5) (number-average molecular weight: 1000, molecular weight distribution: 1.1) (4.20 g) using the method described in the examples of Japanese Unexamined Patent Application, First Publication No. S62-57418.

Next, a dimethylamine aqueous solution (50%, 40 mL) was added to a compound represented by a formula (30) and reacted by being stirred at room temperature for 4 hours. An oil layer was separated from the reaction product obtained after the reaction, dissolved in VERTREL (registered trademark) XF (100 mL) and dehydrated with anhydrous sodium sulfate. After the drying agent was filtered, the filtrate was concentrated, thereby synthesizing a compound (U) (molecular weight: 1202, 3.3 mmol) (3.97 g).

by the following formula (31) (6.4 g, molecular weight: 1264, 5.1 mmol) as an intermediate.

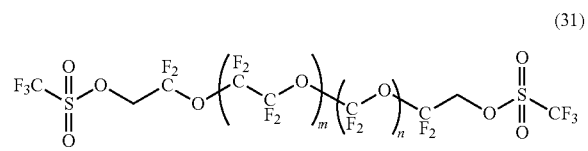
(31)

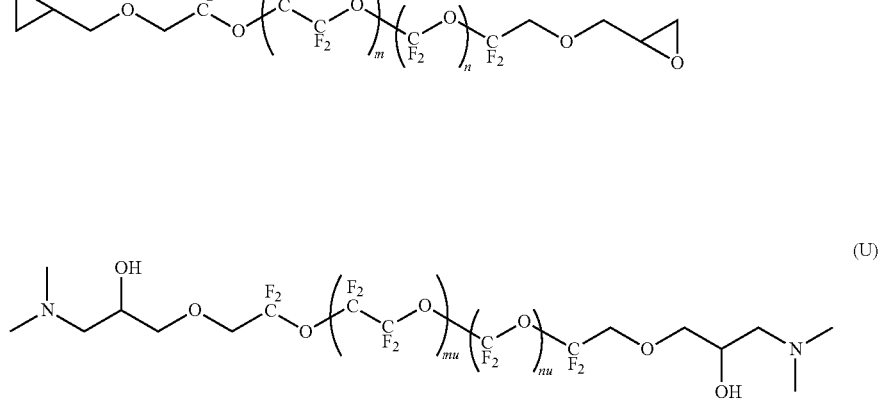
(30)

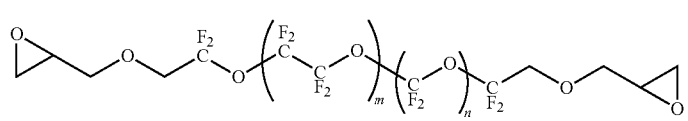
(U)

(In the formula (30), m indicating the average degree of polymerization is 4.5, and n indicating the average degree of polymerization is 4.5.)

(In the formula (U), mu indicating the average degree of polymerization is 4.5, and nu indicating the average degree of polymerization is 4.5.)

$^1$H-NMR measurement of the obtained compound (U) was carried out, and the structure was identified from the following results.

Compound (U); $^1$H-NMR (CDCl$_3$); δ[ppm]=2.11 to 2.19 (1H), 2.32 (6H), 2.37 to 2.50 (1H), 3.51 to 3.74 (2H), 3.78 to 4.03 (4H)

Comparative Example 4

A compound represented by the following formula (V) was synthesized by the following method.

Trifluoromethanesulfonyl chloride (2.5 g) and dimethylaminopyridine (0.92 g) were prepared and stirred at −20° C. Next, a compound represented by HOCH$_2$CF$_2$O (CF$_2$CF$_2$O)$_m$ (CF$_2$O)$_n$CF$_2$CH$_2$OH (m indicating the average degree of polymerization in the formula was 4.5 and n indicating the average degree of polymerization was 4.5) (number-average molecular weight: 1000, molecular weight distribution: 1.1) (5.0 g) was added drop wise and reacted for 2 hours.

After the reaction, the obtained reaction product was returned to room temperature, moved to a separatory funnel containing water (100 mL) and extracted three times with ethyl acetate (100 mL). An organic layer thereof was washed with water and dehydrated with anhydrous sodium sulfate. After the drying agent was filtered, the filtrate was concentrated, and the residue was purified by silica gel column chromatography, thereby obtaining a compound represented (In the formula (31), m indicating the average degree of polymerization is 4.5, and n indicating the average degree of polymerization is 4.5.)

The compound represented by the formula (31) which was the intermediate obtained above (6.0 g, molecular weight: 1264.1, 4.8 mmol), 2-(ethylamino)ethanol (1.3 g, molecular weight: 89.14, 14.2 mmol) and acetonitrile (12.4 mL) were charged into a 100 mL eggplant flask under a nitrogen gas atmosphere and stirred until the composition became uniform at room temperature, and heating under reflux with stirring was carried out for 6 hours.

After the reaction, the obtained reaction product was cooled to 25° C., moved to a separatory funnel containing a saturated sodium hydrogen carbonate solution (100 mL) and extracted three times with ethyl acetate (100 mL). An organic layer thereof was washed with water and dehydrated with anhydrous sodium sulfate. After the drying agent was filtered, the filtrate was concentrated, the residue was purified by silica gel column chromatography, thereby obtaining a compound (V) (in the formula (V), mv indicating the average degree of polymerization was 4.5 and nv indicating the average degree of polymerization was 4.5) (3.78 g, molecular weight: 1144, 3.3 mmol).

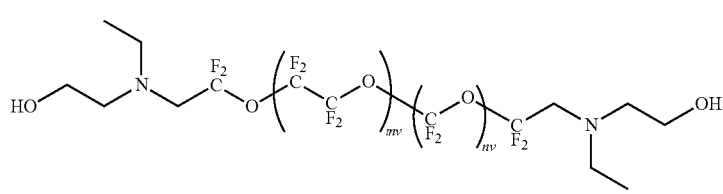

(V)

(In the formula (V), mv indicating the average degree of polymerization is 4.5, and nv indicating the average degree of polymerization is 4.5.)

$^1$H-NMR measurement of the obtained compound (V) was carried out, and the structure was identified from the following results.

Compound (V); $^1$H-NMR (CD$_3$COCD$_3$); δ[ppm]=1.05 (6H), 2.58 to 2.67 (8H), 3.37 to 3.68 (10H)

Comparative Example 5

A compound represented by the following formula (W) was synthesized by the following method.

The same operation as in Example 1 was carried out except that a compound represented by the following formula (32) (3.80 g) was used instead of the compound represented by formula (11) and the compound represented by the formula (26) (0.80 g) was used instead of the compound represented by formula (13), thereby obtaining a compound represented by the following formula (W) (4.02 g).

The compound represented by the formula (32) used in the reaction was synthesized by protecting the primary hydroxyl group in 2,3-epoxy-1-propanol using dihydropyran.

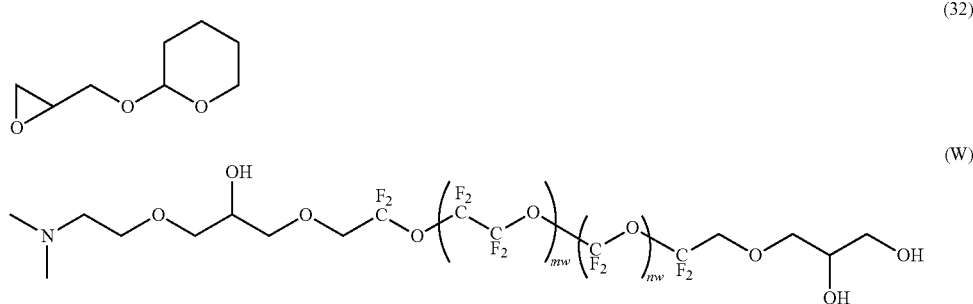

(In the formula (W), mw indicating the average degree of polymerization is 4.5, and nw indicating the average degree of polymerization is 4.5.)

$^1$H-NMR measurement of the obtained compound (W) was carried out, and the structure was identified from the following results.

Compound (W); $^1$H-NMR (CD$_3$COCD$_3$); δ[ppm]=2.25 (6H), 2.46 to 2.48 (2H), 3.41 to 4.54 (19H)

The structures of R$^1$ (R$^5$R$^6$N— and a in the formula (2)), the structures of R$^2$ (b in the formula (3)), the structures of R$^3$ and the structures of R$^4$, when the compounds of Examples 1 to 18 and Comparative Examples 1 to 5 obtained as described above were adapted to the formula (1), are shown in Table 1 to Table 3.

Regarding Comparative Examples 1 to 5, the cells in the column for the structure of R$^1$ (groups corresponding to R$^5$R$^6$N— in the formula (2)) were filled with terminal groups that were disposed at the R$^5$R$^6$N— positions when adapting the compounds of Comparative Examples 1 to 5 to the formula (1).

In addition, the number-average molecular weights (Mn) of the compounds of Examples 1 to 18 and Comparative Examples 1 to 5 were obtained by the above-described $^1$H-NMR and $^{19}$F-NMR measurement. The results are shown in Table 1 to Table 3. It is assumed that, in the values of the average molecular weight of the synthesized compounds, variations of approximately 1 to 5 may exist depending on the molecular weight distributions of the fluoropolyether used as a raw material of the compounds, differences in the operation at the time of synthesizing the compounds and the like.

TABLE 1

| | R$^1$ Formula (2) R$^5$R$^6$N- | a | R$^2$ Formula (3) b | R$^3$ | R$^4$ | Number-average molecular weight (Mn) | Compound |
|---|---|---|---|---|---|---|---|
| Example 1 | pyrrolidine | 2 | 1 | Formula (4) c = 4.5, d = 4.5 | Formula (7) g = 1, h = 1 | 1289 | (A) |
| Example 2 | piperidine | 2 | 1 | Formula (4) c = 4.5, d = 4.5 | Formula (7) g = 1, h = 1 | 1303 | (B) |
| Example 3 | morpholine | 2 | 1 | Formula (4) c = 4.5, d = 4.5 | Formula (7) g = 1, h = 1 | 1305 | (C) |
| Example 4 | azepane | 2 | 1 | Formula (4) c = 4.5, d = 4.5 | Formula (7) g = 1, h = 1 | 1317 | (D) |
| Example 5 | pyrrolidine | 2 | 1 | Formula (4) c = 4.5, d = 4.5 | Formula (7) g = 2, h = 1 | 1363 | (E) |
| Example 6 | piperidine | 2 | 1 | Formula (4) c = 4.5, d = 4.5 | Formula (7) g = 2, h = 1 | 1377 | (F) |
| Example 7 | morpholine | 2 | 1 | Formula (4) c = 4.5, d = 4.5 | Formula (7) g = 2, h = 1 | 1379 | (G) |
| Example 8 | azepane | 2 | 1 | Formula (4) c = 4.5, d = 4.5 | Formula (7) g = 2, h = 1 | 1392 | (H) |
| Example 9 | pyrrolidine | 2 | 2 | Formula (4) c = 4.5, d = 4.5 | Formula (7) g = 2, h = 1 | 1438 | (I) |
| Example 10 | piperidine | 2 | 2 | Formula (4) c = 4.5, d = 4.5 | Formula (7) g = 2, h = 1 | 1452 | (J) |

TABLE 2

| | R$^1$ Formula (2) R$^5$R$^6$N- | a | R$^2$ Formula (3) b | R$^3$ | R$^4$ | Number-average molecular weight (Mn) | Compound |
|---|---|---|---|---|---|---|---|
| Example 11 | morpholine | 2 | 2 | Formula (4) c = 4.5, d = 4.5 | Formula (7) g = 2, h = 1 | 1454 | (K) |
| Example 12 | azepane | 2 | 2 | Formula (4) c = 4.5, d = 4.5 | Formula (7) g = 2, h = 1 | 1466 | (L) |

TABLE 2-continued

| | R$^1$ Formula (2) R$^5$R$^6$N- | a | R$^2$ Formula (3) b | R$^3$ | R$^4$ | Number-average molecular weight (Mn) | Compound |
|---|---|---|---|---|---|---|---|
| Example 13 | pyrrolidinyl | 3 | 2 | Formula (4) c = 4.5, d = 4.5 | Formula (10) k = 2, l = 1 | 1466 | (M) |
| Example 14 | dimethylamino | 2 | 1 | Formula (4) c = 4.5, d = 4.5 | Formula (7) g = 1, h = 1 | 1263 | (N) |
| Example 15 | dimethylamino | 3 | 1 | Formula (4) c = 4.5, d = 4.5 | Formula (7) g = 1, h = 1 | 1277 | (O) |
| Example 16 | diethylamino | 2 | 2 | Formula (4) c = 4.5, d = 4.5 | Formula (7) g = 1, h = 1 | 1365 | (P) |
| Example 17 | pyrrolidinyl | 2 | 1 | Formula (4) c = 7.1 | Formula (7) g = 1, h = 1 | 1289 | (Q) |
| Example 18 | pyrrolidinyl | 2 | 1 | Formula (6) f = 4.4 | Formula (7) g = 1, h = 1 | 1289 | (R) |

TABLE 3

| | R$^1$ Formula (2) Group corresponding to R$^5$R$^6$N- | a | Presence or absence of ether bond | R$^2$ Formula (3) b | R$^3$ | R$^4$ | Number-average molecular weight (Mn) | Compound |
|---|---|---|---|---|---|---|---|---|
| Comparative Example 1 | pyridinyl | 2 | Present | 1 | Formula (4) c = 4.5, d = 4.5 | Formula (7) g = 1, h = 1 | 1297 | (S) |
| Comparative Example 2 | dimethylamino | 2 | Present | — | Formula (4) c = 4.5, d = 4.5 | Formula (7) g = 1, h = 1 | 1205 | (T) |
| Comparative Example 3 | dimethylamino | — | Absent | 1 | Formula (4) c = 4.5, d = 4.5 | — | 1202 | (U) |
| Comparative Example 4 | HO-CH$_2$CH$_2$-N(ethyl)- | — | Absent | — | Formula (4) c = 4.5, d = 4.5 | — | 1144 | (V) |
| Comparative Example 5 | dimethylamino | 2 | Present | 1 | Formula (4) c = 4.5, d = 4.5 | — | 1219 | (W) |

Next, solutions for forming a lubricating layer were prepared using the compounds obtained in Examples 1 to 18 and Comparative Examples 1 to 5 by a method to be described below. In addition, lubricating layers of magnetic recording media were formed using the obtained solutions for forming a lubricating layer by a method to be described below, and magnetic recording media of Examples 1 to 18 and Comparative Examples 1 to 5 were obtained.

Solutions for Forming Lubricating Layer

The compounds obtained in Examples 1 to 18 and Comparative Examples 1 to 5 were each dissolved in VERTREL (registered trademark) XF (trade name, manufactured by Dupont-Mitsui Fluorochemicals Co., Ltd.), which is a fluorine-based solvent, diluted with VERTREL XF such that the film thicknesses became 9 Å to 10 Å when applied onto protective layers and used as solutions for forming a lubricating layer.

Magnetic Recording Media

Magnetic recording media each having an adhesive layer, a soft magnetic layer, a first underlayer, a second underlayer, a magnetic layer and a protective layer sequentially provided on a substrate having a diameter of 65 mm were prepared. As the protective layer, a carbon layer was used.

The solutions for forming, a lubricating layer of Examples 1 to 18 and Comparative Examples 1 to 5 were each applied onto the protective layers of the magnetic recording media in which the individual layers up to the protective layer had been formed by the dipping method. The dipping method was carried out under conditions of an immersion speed of 10 mm/sec, an immersion time of 30 seconds and a lifting speed of 1.2 mm/sec.

After that, the magnetic recording media to which the solutions for forming a lubricating layer had been applied were put into a thermostatic chamber (120° C.) and heated for 10 minutes to remove the solvent in the solutions for forming a lubricating layer, thereby forming lubricating layers on the protective layers and obtaining magnetic recording media.

Film Thickness Measurement

The film thicknesses of the lubricating layers in the magnetic recording media of Examples 1 to 18 and Comparative Examples 1 to 5 obtained as described above were measured using FT-IR (trade name: Nicolet iS50, manufactured by Thermo Fisher Scientific). The results are shown in Table 4.

TABLE 4

| | Compound | Film thickness (A) | Friction coefficient increase time | Amount of Si adsorbed | Comprehensive evaluation |
|---|---|---|---|---|---|
| Example 1 | (A) | 9.0 | AA | 0.76 | A |
| Example 2 | (B) | 9.1 | A | 0.66 | A |
| Example 3 | (C) | 9.1 | AA | 0.80 | A |
| Example 4 | (D) | 9.0 | A | 0.58 | A |
| Example 5 | (E) | 9.0 | AA | 0.42 | AA |
| Example 6 | (F) | 9.2 | A | 0.39 | A |
| Example 7 | (G) | 9.0 | AA | 0.48 | AA |
| Example 8 | (H) | 9.0 | AA | 0.44 | AA |
| Example 9 | (I) | 9.1 | AA | 0.48 | AA |
| Example 10 | (J) | 9.0 | AA | 0.38 | AA |
| Example 11 | (K) | 9.0 | AA | 0.41 | AA |

TABLE 4-continued

| | Compound | Film thickness (A) | Friction coefficient increase time | Amount of Si adsorbed | Comprehensive evaluation |
|---|---|---|---|---|---|
| Example 12 | (L) | 9.0 | AA | 0.43 | AA |
| Example 13 | (M) | 9.0 | AA | 0.44 | AA |
| Example 14 | (N) | 9.0 | A | 0.66 | A |
| Example 15 | (O) | 9.1 | A | 0.52 | A |
| Example 16 | (P) | 9.0 | A | 0.58 | A |
| Example 17 | (Q) | 9.0 | AA | 0.74 | A |
| Example 18 | (R) | 9.0 | AA | 0.77 | A |
| Comparative Example 1 | (S) | 9.1 | B | 1.00 | B |
| Comparative Example 2 | (T) | 9.0 | B | 1.64 | C |
| Comparative Example 3 | (U) | 9.0 | B | 2.01 | C |
| Comparative Example 4 | (V) | 9.0 | B | 2.13 | C |
| Comparative Example 5 | (W) | 9.1 | B | 1.47 | C |

Next, wear resistance tests were carried out as described below on the magnetic recording media of Examples 1 to 18 and Comparative Examples 1 to 5.

Wear Resistance Test

An alumina sphere having a diameter of 2 mm, which was a contact, was slid on the lubricating layers of the magnetic recording media using a pin-on disc-type friction wear tester at a load of 40 gf and a sliding speed of 0.25 m/sec, and the friction coefficients of the surfaces of the lubricating layers were measured. In addition, the sliding times until the friction coefficients of the surfaces of the lubricating layers sharply increased were measured. The sliding time until the friction coefficient sharply increased was measured four times for the lubricating layer of each magnetic recording medium, and the average value (time) was used as an index of the wear resistance of a lubricant coating. The results of the magnetic recording media for which the compounds of Examples 1 to 18 and Comparative Examples 1 to 5 were used are shown in Table 4. The friction coefficient increase times were evaluated as described below.

AA (Excellent): 650 seconds or longer
A (Favorable): 550 seconds or longer and shorter than 650 seconds
B (Permissible): 450 seconds or longer and shorter than 550 seconds The time until the friction coefficient sharply increases can be used as an index of the wear resistance of the lubricating layers for a reason to be described below. The reason is that the use of the magnetic recording medium leads to wear of the lubricating layer in the magnetic recording medium, and, once the lubricating layer disappears due to the wear, the contact and the protective layer come into direct contact with each other, and the friction coefficient sharply increases. The time until the friction coefficient sharply increases is also considered to correlate with friction tests.

As shown in Table 4, in the magnetic recording media of Examples 1 to 18, the sliding times until the friction coefficient sharply increased were long and the wear resistance was favorable compared with the magnetic recording media of Comparative Examples 1 to 5. In addition, from the results of Examples 1 to 8, it was confirmed that, in a case where $R^5R^6N$— in the formula (2) was a pyrrolidine group or a morpholine group, a lubricating layer being particularly excellent in wear resistance could be obtained.

Chemical Substance Resistance Test

Contamination of the magnetic recording media due to art environmental substance that generates a contamination substance in high-temperature environments was inspected by an evaluation method to be described below. In the evaluation method to be described below, Si ions were used as the environmental substance, and the amount of Si adsorbed was measured as the amount of the contamination substance that was generated by the environmental substance and contaminated the magnetic recording media.

Specifically, the magnetic recording medium, which was an evaluation subject, was held under a high-temperature environment of 85° C. and a humidity of 0% in the presence of siloxane-based Si rubber for 240 hours. Next, the amount of Si present on and adsorbed to the surface of the magnetic recording medium was analyzed and measured using secondary-ion mass spectrometry (SIMS), and the degree of contamination by Si ions was evaluated from the amount of Si adsorbed. The evaluation of the amount of Si adsorbed was evaluated using a numerical value relative to the result of Comparative Example 1 regarded as 1.00. The results are shown in Table 4. As the numerical value becomes smaller, the chemical substance resistance becomes superior.

As shown in Table 4, in the magnetic recording media of Examples 1 to 18, it was clarified that the amounts of Si adsorbed were small and the magnetic recording media were less likely to be contaminated by the environmental substance under the high-temperature environments compared with the magnetic recording media of Comparative Examples 1 to 5.

In addition, from the results of Examples 1 to 8, it was confirmed that lubricating layers having superior chemical substance resistance could be obtained in a case where g was 2 in the formula (7) as $R^4$ compared with when g was 1.

In addition, the compounds and magnetic recording media of Examples 1 to 18 and Comparative Examples 1 to 5 were comprehensively evaluated based on criteria to be described below. The results are shown in Table 4.

AA (Excellent): The friction coefficient increase time is evaluated as AA (excellent) and the amount of Si adsorbed is less than 0.51.

A (Favorable): The friction coefficient increase time is evaluated as AA (excellent) or A (favorable) and the amount of Si adsorbed is less than 1.01.

B (Permissible): The friction coefficient increase time is evaluated as B (permissible) and the amount of Si adsorbed is less than 1.01.

C (Impermissible): The friction coefficient increase time is evaluated as B (permissible) and the amount of Si adsorbed is 1.01 or more.

As shown in Table 4, in the magnetic recording media of Examples 1 to 18 in which the compound represented by the formula (1) was used, the comprehensive evaluation was AA (excellent) or A (favorable) and excellent wear resistance and chemical substance resistance were obtained.

In contrast, the comprehensive evaluation of Comparative Example 1 was B (permissible) and the comprehensive evaluations of Comparative Examples 2 to 5 were C (impermissible).

In more detail, in Comparative Example 1 in which the compound containing a pyridine group was used instead of the structure of $R^1$ in the formula (1) ($R^5R^6N$— in the formula (2)), the result of the wear resistance test and the result of the chemical substance resistance test were poor compared with those of Examples 1 to 18.

From this fact, it was confirmed that the structure of $R^1$ in the formula (1) ($R^5R^6N$— in the formula (2)) contributed to improvement in the wear resistance and chemical substance resistance of lubricating layers.

In addition, in Comparative Example 2 in which the compound having no structure of $R^2$ in the formula (1) was used, the result of the wear resistance test and the result of the chemical substance resistance test were poor compared with those of Examples 1 to 18. From this fact, it was confirmed that the structure of $R^2$ in the formula (1) contributed to improvement in the wear resistance and chemical substance resistance of lubricating layers.

In addition, in Comparative Example 3 in which the compound having a structure in which the tertiary amines were bonded to both terminals of the PFPE chain through divalent linking groups having an ether bond and a hydroxyl group, and not having the structure of —$(CH_2)_a$—O— in the formula (2) of $R^1$ and the structure of $R^4$, which are included in the formula (1), was used, the result of the wear resistance test and the result of the chemical substance resistance test were poor compared with those of Examples 1 to 18.

In addition, in Comparative Example 4 in which the compound having a structure in which the tertiary amines having a hydroxyl group were bonded to both terminals of the PFPE chain, and not having the structure of —$(CH_2)_a$—O— in the formula (2) of $R^1$, the structure of $R^2$ and the structure of $R^4$, which are included in the formula (1), was used, the result of the wear resistance test and the result of the chemical substance resistance test were poor compared with those of Examples 1 to 18.

In addition, among Comparative Example 1 to Comparative Example 5, Comparative Example 3 and Comparative Example 4 were examples in which, particularly, the amount of Si adsorbed was large and the result of the chemical substance resistance test was poor.

In addition, in Comparative Example 5 in which the compound having a terminal group in which two hydroxyl groups each bonded to different carbon atoms, and the carbon atoms to which the hydroxyl groups bonded were bonded to each other at one end of the PFPE chain instead of the structure of $R^4$ in the formula (1) was used, the result of the wear resistance test and the result of the chemical substance resistance test were poor.

From this fact, it was confirmed that the structure of $R^4$ in the formula (1) contributed to improvement in the wear resistance and chemical substance resistance of lubricating layers.

INDUSTRIAL APPLICABILITY

The present invention provides a preferable fluorine-containing ether compound as a material for lubricants for magnetic recording media capable of forming lubricating layers having excellent chemical substance resistance and wear resistance in spite of a thin thickness.

The use of a lubricant for a magnetic recording medium containing the fluorine-containing ether compound of the present invention makes it possible to form lubricating layers having excellent wear resistance and chemical substance resistance in spite of a thin thickness.

REFERENCE SIGNS LIST

10 Magnetic recording medium
11 Substrate
12 Adhesive layer
13 Soft magnetic layer 14 First underlayer
15 Second underlayer
16 Magnetic layer
17 Protective layer
18 Lubricating layer

The invention claimed is:

1. A fluorine-containing ether compound represented by the following formula (1),

(in the formula (1), $R^3$ is a perfluoropolyether chain; $R^1$ is represented by the following formula (2), a in the formula (2) is an integer of 2 or 3, in the formula (2), $R^5$ and $R^6$ are the same or different substituents, and $R^5$ and $R^6$ may form a ring structure together with a nitrogen atom; $R^2$ is represented by the following formula (3), and b in the formula (3) is an integer of 1 to 3; $R^4$ is a terminal group having two or three polar groups, in which individual polar groups bond to different carbon atoms and the carbon atoms to which the polar groups bond are bonded to each other through a linking group having a carbon atom to which the polar groups do not bond),

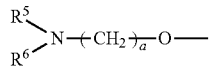 (2)

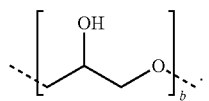 (3)

2. The fluorine-containing ether compound according to claim 1,
wherein $R^5$ and $R^6$ are each independently a saturated aliphatic group having one to four carbon atoms or $R^5$ and $R^6$ form a five to seven-membered ring together with a nitrogen atom.

3. The fluorine-containing ether compound according to claim 1,
wherein $R^5R^6N-$ in the formula (2) is a dimethylamino group or a diethylamino group.

4. The fluorine-containing ether compound according to claim 1,
wherein $R^5R^6N-$ in the formula (2) is any one group selected from a pyrrolidine group, a piperidine group, a morpholine group, and a hexamethyleneimine group.

5. The fluorine-containing ether compound according to claim 1,
wherein the $R^3$ is any of the following formulae (4) to (6), $-CF_2O-(CF_2CF_2O)_c-(CF_2O)_d-CF_2-$ (4)

(c and d in the formula (4) indicate average degrees of polymerization and each represents 0 to 30; here, there is no case where c and d become 0 at the same time), $-CF(CF_3)-(OCF(CF_3)CF_2)_e-OCF(CF_3)-$ (5)

(e in the formula (5) indicates an average degree of polymerization and represents 0.1 to 30), $-CF_2CF_2O-(CF_2CF_2CF_2O)_f-CF_2CF_2-$ (6)

(f in the formula (6) indicates an average degree of polymerization and represents 0.1 to 30).

6. The fluorine-containing ether compound according to any claim 1
wherein the polar group in the $R^4$ is a hydroxyl group.

7. The fluorine-containing ether compound according to claim 1,
wherein the $R^4$ is a terminal group of any of the following formulae (7) to (10),

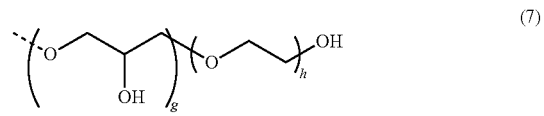 (7)

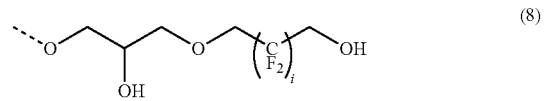 (8)

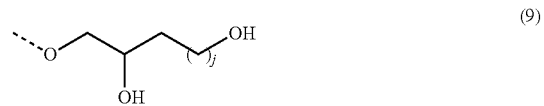 (9)

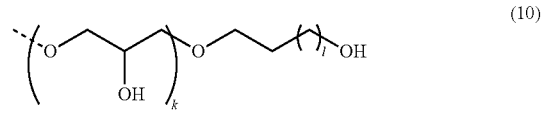 (10)

(in the formula (7), g represents an integer of 1 or 2, and h represents an integer of 1 to 5),
(in the formula (8), i represents an integer of 2 to 5),
(in the formula (9), j represents an integer of 1 to 5), and
(in the formula (10), k represents an integer of 1 or 2, and l represents an integer of 1 or 2).

8. The fluorine-containing ether compound according to claim 1,
wherein a number-average molecular weight thereof is within a range of 500 to 10000.

9. The fluorine-containing ether compound according to claim 1,
wherein the compound represented by the formula (1) is any of compounds represented by the following formulae (A) to (D), (N) and (O),

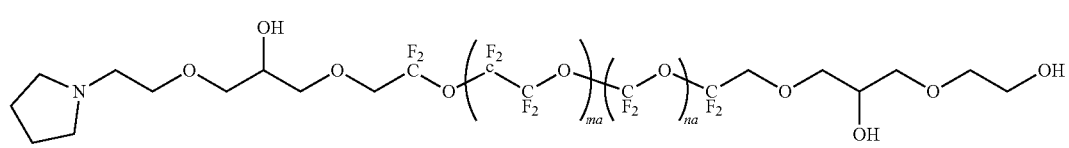 (A)

-continued

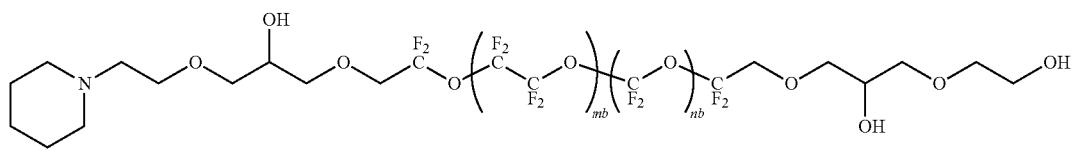
(B)

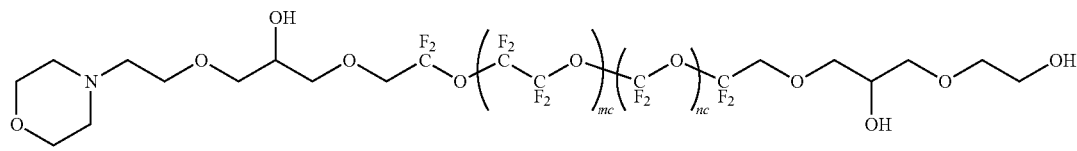
(C)

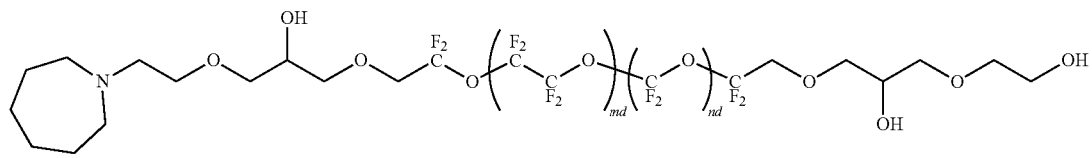
(D)

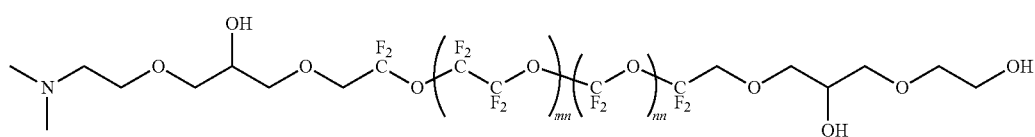
(N)

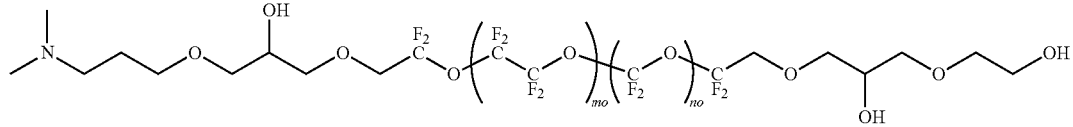
(O)

(in the formula (A), ma and na indicate average degrees of polymerization, ma represents 1 to 30, and na represents 0 to 30), (in the formula (B), mb and nb indicate average degrees of polymerization, mb represents 1 to 30, and nb represents 0 to 30), (in the formula (C), mc and nc indicate average degrees of polymerization, mc represents 1 to 30, and nc represents 0 to 30), (in the formula (D), md and nd indicate average degrees of polymerization, md represents 1 to 30, and nd represents 0 to 30), (in the formula (N), mn and nn indicate average degrees of polymerization, mn represents 1 to 30, and nn represents 0 to 30), and (in the formula (O), mo and no indicate average degrees of polymerization, mo represents 1 to 30, and no represents 0 to 30).

10. A lubricant for a magnetic recording medium, comprising:
   the fluorine-containing ether compound according to claim 1.

11. A magnetic recording medium comprising at least:
   a magnetic layer;
   a protective layer; and
   a lubricating layer sequentially provided on a substrate,
   wherein the lubricating layer contains the fluorine-containing ether compound according to claim 1.

12. The magnetic recording medium according to claim 11,
   wherein the lubricating layer has an average film thickness of 0.5 nm to 2 nm.

* * * * *